United States Patent [19]
Black et al.

[11] Patent Number: 5,629,285
[45] Date of Patent: May 13, 1997

[54] INHIBITORS OF TNF-α SECRETION

[75] Inventors: Roy A. Black; Jeffrey N. Fitzner; Paul R. Sleath, all of Seattle, Wash.

[73] Assignee: Immunex Corporation, Seattle, Wash.

[21] Appl. No.: 651,363

[22] Filed: May 22, 1996

Related U.S. Application Data

[60] Division of Ser. No. 292,547, Aug. 18, 1994, which is a continuation-in-part of Ser. No. 110,601, Aug. 23, 1993, abandoned.

[51] Int. Cl.$^6$ .......................... A61K 38/00; A61K 38/16; A61K 31/66; A61K 31/215
[52] U.S. Cl. .................. 514/2; 514/7; 514/119; 514/507; 514/563; 530/331
[58] Field of Search .................. 514/7, 2, 507, 514/563, 119

[56] References Cited

U.S. PATENT DOCUMENTS

| | | | |
|---|---|---|---|
| 4,382,081 | 5/1983 | Sundeen et al. | 514/18 |
| 4,599,361 | 7/1986 | Dickens et al. | 514/575 |
| 4,681,894 | 7/1987 | Murray et al. | 514/507 |
| 4,943,587 | 7/1990 | Cetenko et al. | 514/415 |
| 5,093,356 | 3/1992 | Girard et al. | 514/432 |
| 5,110,831 | 5/1992 | Magolda et al. | 514/645 |
| 5,114,953 | 5/1992 | Galardy et al. | 514/323 |
| 5,145,858 | 9/1992 | Adams et al. | 514/318 |
| 5,304,549 | 4/1994 | Broadhurst et al. | 514/80 |
| 5,304,604 | 4/1994 | Davidson et al. | 514/238.2 |

FOREIGN PATENT DOCUMENTS

| | | |
|---|---|---|
| 0054862A1 | 6/1982 | European Pat. Off. |
| 0231081B1 | 8/1987 | European Pat. Off. |
| 0358660 | 9/1988 | European Pat. Off. |
| 0401963A1 | 12/1990 | European Pat. Off. |
| 0438223A1 | 7/1991 | European Pat. Off. |
| 0489577A1 | 6/1992 | European Pat. Off. |
| 0498665A1 | 8/1992 | European Pat. Off. |
| 0519748A2 | 12/1992 | European Pat. Off. |
| 0534363A2 | 3/1993 | European Pat. Off. |
| 0534396A2 | 3/1993 | European Pat. Off. |
| 0534492A1 | 3/1993 | European Pat. Off. |
| 2268934 | 1/1994 | United Kingdom |
| WO88/06890 | 9/1988 | WIPO |
| WO91/02540 | 3/1991 | WIPO |
| WO92/02822 | 2/1992 | WIPO |
| WO92/09563 | 6/1992 | WIPO |
| WO92/09556 | 6/1992 | WIPO |
| WO92/14462 | 9/1992 | WIPO |
| WO92/22523 | 12/1992 | WIPO |
| WO93/15045 | 8/1993 | WIPO |
| WO93/15044 | 8/1993 | WIPO |

OTHER PUBLICATIONS

Spatola, et al., *CA Selects: Amino Acids, Peptides & Proteins*, Issue 17:13 (1993).
Davies, et al., *Cancer Research*, Issue 53, 2087–2091 (1993).
Nixon, et al., *Int. Journ. Tiss. Reac.*, XIII(5): 237–243 (1991).
Scuderi, P., *J. of Immunology*, 143, No. 1, 168–173 (1989).
Kriegler et al., *Cell*, 53: 45–53 (1988).
Spatola, et al., *Tetrahedron*, vol. 44, No. 3, 821–833 (1988).
Hudson, et al., *Int. J. Peptide Protein Research*, 14: 177–185 (1985).
Spatola et al., *Vega Data*, vol. 1, Issue 3, 267 (1983).
Hann, M., *The Royal Society of Chemistry*, 307–314 (1982).
Morely, J.S., *TIPS*, 463–468 (1980).
Gearing et al., *Nature*, 370:555 (1994).
McGeehan, et al., *Nature*, 370: 558 (1994).
Schultz, et al., *Invest. Ophtham. & Visual Sci.* vol. 33, No. 12, 3325 (1992).
Andrews, et al., *Agents Actions* 37: 147 (1992).
Black, et al., *Nature*, 370: 218 (1994).
Han, et al., *J. Exp. Med.*, 172: 391 (1990).
Sampaio, et al., *J. Exp. Med.*, 173: 699 (1991).

*Primary Examiner*—Joseph Conrad
*Attorney, Agent, or Firm*—Stephen L. Malaska

[57] ABSTRACT

Compounds and methods are disclosed that are useful in inhibiting the TNF-α converting enzyme (TACE) responsible for cleavage of TNF-α precursor to provide biologically active TNF-α. The compounds employed in the invention are peptidyl derivatives having active groups capable of inhibiting TACE such as, hydroxamates, thiols, phosphoryls and carboxyls.

19 Claims, No Drawings

INHIBITORS OF TNF-α SECRETION

CROSS-REFERENCE TO RELATED APPLICATIONS

This application is a divisional of application Ser. No. 08/292,547 filed Aug. 18, 1994 which is a continuation-in-part of application Ser. No. 08/110,601, filed Aug. 23, 1993, now abandoned.

FIELD OF THE INVENTION

The invention pertains to compounds which are inhibitors of metalloproteases and, in particular, to compounds which inhibit the TNF-α converting enzyme.

BACKGROUND OF THE INVENTION

Tumor necrosis factor-α (TNF-α, also known as cachectin) is a mammalian protein capable of inducing a variety of effects on numerous cell types. TNF-α was initially characterized by its ability to cause lysis of tumor cells and is produced by activated cells such as mononuclear phagocytes, T-cells, B-cells, mast cells and NK cells. In mononuclear phagocytes, TNF-α is initially synthesized as a membrane-bound protein of approximately 26 kD. A 17 kD fragment of the 26 kD membrane-bound TNF-α is "secreted" and combines with two other secreted TNF-α molecules to form a circulating 51 kD homotrimer. TNF-α is a principal mediator of the host response to gram-negative bacteria. Lipopolysaccharide (LPS, also called endotoxin), derived from the cell wall of gram-negative bacteria, is a potent stimulator of TNF-α synthesis. Because the deleterious effects which can result from an over-production or an unregulated-production of TNF are extremely serious, considerable efforts have been made to control or regulate the serum level of TNF. An important part in the effort to effectively control serum TNF levels is the understanding of the mechanism of TNF biosynthesis.

The mechanism by which TNF-α is secreted has only been recently elucidated. Kriegler et al. *Cell*, 53, 45–53, (1988) conjectured that TNF-α "secretion" is due to the cleaving of the 26 kD membrane-bound molecule by a proteolytic enzyme or protease. Scuderi et. al., *J. Immunology*, 143, 168–173 (1989), suggested that the release of TNF-α from human leukocyte cells is dependent on one or more serine proteases, e.g., a leukocyte elastase or trypsin. A serine protease inhibitor, p-toluenesulfonyl-L-arginine methyl ester, was found to suppress human leukocyte TNF release in a concentration-dependent manner. Scuderi et. suggested that the arginine methyl ester competes for the arginine-binding site in the enzyme's reactive center and thereby blocks hydrolysis. The lysine and phenylalanine analogs of the inhibitor reportedly failed to mimic the arginine methyl ester.

We have discovered that the protease which causes the cleavage of the TNF-α molecule into the 17 kD protein is, in fact, a metalloprotease which is believed to reside in the plasma membrane of cells producing TNF-α. The physico-chemical characteristics of the enzyme have not been published.

Most, but not all, proteases recognize a specific amino acid sequence. Some proteases primarily recognize residues located N-terminal of the cleaved bond, some recognize residues located C-terminal of the cleaved bond, and some proteases recognize residues on both sides of the cleaved bond. Metalloprotease enzymes utilize a bound metal ion, generally $Zn^{2+}$, to catalyze the hydrolysis of the peptide bond. Metalloproteases are implicated in joint destruction (the matrix metalloproteases), blood pressure regulation (angiotensin converting enzyme), and regulation of peptide-hormone levels (neutral endopeptidase-24.11).

Numerous inhibitors have been developed against the previously described metalloproteases. A general family of inhibitors against matrix-metalloproteases, and in particular collagenase, is reported in WO 92/09563. This document shows compounds having the general structure of a reverse hydroxamate—or a hydroxyurea—linked via an amide to an amino acid derivative, such as tryptophan or 2-naphthyl alanine. Inhibitors of collagenase are also reported in WO 88/06890; these compounds contain sulfhydryl moieties as well as phenylalanine and tryptophan analogs. Collagenase inhibitors are reported in WO 92/09556 and U.S. Pat. No. 5,114,953 and possess hydroxamate moities and fused or conjugated bicycloaryl substituents. The myriad potential gelatinase inhibitors covered by the generic formula in EPA 489,577 are amino acid derivatives optionally possessing a hydroxamate group. Hydroxamate derivatives useful as angiotensin converting enzyme (ACE) inhibitors are reported in EPO 498,665.

Inhibition of the TNF-α converting enzyme (hereinafter referred to as "TACE"), a novel metalloprotease, inhibits release of TNF-α into the serum and other extracellular spaces. TACE inhibitors would therefore have clinical utility in treating conditions characterized by over-production or unregulated production of TNF-α. A particularly useful TACE inhibitor for certain pathological conditions would selectively inhibit TACE while not affecting TNF-β (also known as lymphotoxin) serum levels. The over-production or unregulated production of TNF-α has been implicated in certain conditions and diseases, for example:

I. Systemic Inflammatory Response Syndrome, which includes:
Sepsis syndrome
    gram positive sepsis
    gram negative sepsis
    culture negative sepsis
    fungal sepsis
    neutropenic fever
    urosepsis
    meningococcemia
Trauma/hemorrhage
Burns
Ionizing radiation exposure
Acute pancreatitis
Adult respiratory distress syndrome.
II. Reperfusion Injury, which includes:
Post pump syndrome
Ischemia-reperfusion injury
   III. Cardiovascular Disease, which includes:
Cardiac stun syndrome
Myocardial infarction
Congestive heart failure
   IV. Infectious Disease, which includes:
HIV infection/HIV neuropathy
Meningitis
Hepatitis
Septic arthritis
Peritonitis
Pneumonia
Epiglottitis
*E. coli* 0157:H7
Hemolytic uremic syndrome/thrombolytic thrombocytopenic purpura Malaria
Dengue hemorrhagic fever
Leishmaniasis
Leprosy
Toxic shock syndrome
Streptococcal myositis
Gas gangrene
Mycobacterium tuberculosis
Mycobacterium avium intracellulare
Pneumocystis carinii pneumonia
Pelvic inflammatory, disease
Orchitis/epidydimitis
Legionella
Lyme disease
Influenza A
Epstein-Barr Virus
Vital-associated hemaphagocytic syndrome
Vital encephalitis/aseptic meningitis
  V. Obstetrics/Gynecology, including:
Premature labor
Miscarriage
Infertility
  VI. Inflammatory Disease/Autoimmunity, which includes:
Rheumatoid arthritis/seronegative arthropathies
Osteoarthritis
Inflammatory bowel disease
Systemic lupus erythematosis
Iridocyclitis/uveitis/optic neuritis
Idiopathic pulmonary fibrosis
Systemic vasculitis/Wegener's granulomatosis
Sarcoidosis
Orchitis/vasectomy reversal procedures
  VII. Allergic/Atopic Diseases, which includes:
Asthma
Allergic rhinitis
Eczema
Allergic contact dermatitis
Allergic conjunctivitis
Hypersensitivity pneumonitis
  VIII. Malignancy, which includes:
ALL
AML
CML
CLL
Hodgkin's disease, non-Hodgkin's lymphoma
MM
Kaposi's sarcoma
Colorectal carcinoma
Nasopharyngeal carcinoma
Malignant histiocytosis
Paraneoplastic syndrome/hypercalcemia of malignancy
  IX. Transplants, including:
Organ transplant rejection
Graft-versus-host disease
  X. Cachexia
  XI. Congenital, which includes:
Cystic fibrosis
Familial hematophagocytic lymphohistiocytosis
Sickle cell anemia
  XII. Dermatologic, which includes:
Psoriasis
Alopecia
  XIII. Neurologic, which includes:
Multiple sclerosis
Migraine headache
  XIV. Renal, which includes:
Nephrotic syndrome
Hemodialysis
Uremia
  XV. Toxicity, which includes:
OKT3 therapy
Anti-CD3 therapy
Cytokine therapy
Chemotherapy
Radiation therapy
Chronic salicylate intoxication
  XVI. Metabolic/Idiopathic, which includes:
Wilson's disease
Hemachromatosis
Alpha-1-antitrypsin deficiency
Diabetes
Hashimoto's thyroiditis
Osteoporosis
Hypothalamic-pituitary-adrenal axis evaluation
Primary biliary cirrhosis Inhibitors of TACE would prevent the cleavage of cell-bound TNF-α thereby reducing the level of TNF-α in serum and tissues. Such inhibitors would be of significant clinical utility and could be potential therapeutics for treating the above TNF-α-related disorders.

SUMMARY OF THE INVENTION

The invention relates to compounds of formula I:

$$X-[CH]_m-\underset{R^1}{CH}-\underset{R^2}{\overset{O}{\overset{\|}{C}}}-\underset{H}{N}-\underset{R^3}{CH}-\overset{O}{\overset{\|}{C}}-[A]_n-\underset{H}{N}-B-NH_2 \quad (I)$$

wherein:

X is hydroxamic acid, thiol, phosphoryl or carboxyl;
m is 0, 1 or 2;
$R^1$, $R^2$ and $R^3$ each independent of the other is hydrogen, alkylene(cycloalkyl), $OR^4$, $SR^4$, $N(R^4)(R^5)$, halogen, substituted or unsubstituted $C_1$ to $C_8$ alkyl, $C_1$ to $C_8$ alkylenearyl, aryl, a protected or unprotected side chain of a naturally occurring α-amino acid; or the group $-R^6R^7$, wherein $R^6$ is substituted or unsubstituted $C_1$ to $C_8$ alkyl and $R^7$ is $OR^4$, $SR^4$, $N(R^4)(R^5)$ or halogen, wherein $R^4$ and $R^5$ are, each independent of the other, hydrogen or substituted or unsubstituted $C_1$ to $C_8$ alkyl;
n is 0, 1 or 2;
provided that when n is 1, A is a protected or an unprotected α-amino acid radical;
when n is 2, A is the same or different protected or unprotected α-amino acid radical; and
B is unsubstituted or substituted $C_2$ to $C_8$ alkylene;
and the pharmaceutically acceptable salts thereof.

The compounds of formula I are useful as metalloprotease inhibitors, and particularly useful as inhibitors of the TNF-α convening enzyme (TACE).

The invention also relates to a method of treating a mammal having a disease characterized by an overproduction or an unregulated production of TNF-α. The method comprises the steps of administering to the mammal a composition comprising an effective amount of a biologically active compound of formula II:

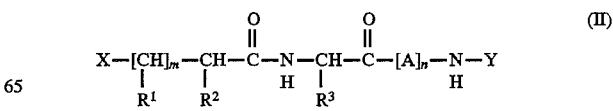

wherein:

X is hydroxamic acid, thiol, phosphoryl or carboxyl;

m is 0, 1 or 2;

$R^1$, $R^2$ and $R^3$ each independent of the other is hydrogen, alkylene(cycloalkyl), $OR^4$, $SR^4$, $N(R^4)(R^5)$, halogen, substituted or unsubstituted $C_1$ to $C_8$ alkyl, $C_1$ to $C_8$ alkylenearyl, aryl, a protected or unprotected side chain of a naturally occurring α-amino acid; or the group —$R^6R^7$, wherein $R^6$ is $C_1$ to $C_8$ alkyl and $R^7$ is $OR^4$, $SR^4$, $N(R^4)(R^5)$ or halogen, wherein $R^4$ and $R^5$ are each, independent of the other, hydrogen or substituted or unsubstituted $C_1$ to $C_8$ alkyl;

n is 0, 1 or 2;

Y is hydrogen, unsubstituted or substituted $C_1$ to $C_8$ alkyl, alkylene(cycloalkyl), the group —$R^8$—$COOR^9$ or the group —$R^{10}N(R^{11})(R^{12})$; wherein $R^8$ is $C_1$ to $C_8$ alkylene; $R^9$ is hydrogen or $C_1$ to $C_8$ alkyl; $R^{10}$ is unsubstituted or substituted $C_1$ to $C_8$ alkylene; and $R^{11}$ and $R^{12}$ are each, independent of the other, hydrogen or $C_1$ to $C_8$ alkyl;

provided that when n is 1, A is a protected or an unprotected α-amino acid radical; and when n is 2, A is the same or different protected or unprotected α-amino acid radical; and the pharmaceutically acceptable salts thereof;

wherein the compound is capable of reducing serum TNF-α levels by at least 80% when administered at 25 mg/kg in a murine model of LPS-induced sepsis syndrome; and a pharmaceutically acceptable carrier.

The discovery of useful inhibitors of the TACE metalloprotease has led to the discovery of further embodiments of the invention, including pharmaceutical compositions for treating the above-listed disorders comprising a compound according to formula II and protein having TNF-binding activity.

DETAILED DESCRIPTION OF THE INVENTION

The invention is directed to a compound of formula I:

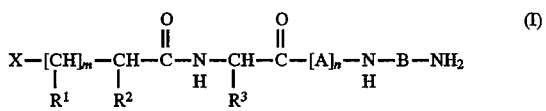

wherein:

X is hydroxamic acid, thiol, phosphoryl or carboxyl;

m is 0, 1 or 2;

$R^1$, $R^2$ and $R^3$ each independent of the other is hydrogen, alkylene(cycloalkyl), $OR^4$, $SR^4$, $N(R^4)(R^5)$, halogen, substituted or unsubstituted $C_1$ to $C_8$ alkyl, $C_1$ to $C_8$ alkylenearyl, aryl, a protected or unprotected side chain of a naturally occurring α-amino acid; or the group —$R^6R^7$, wherein $R^6$ is substituted or unsubstituted $C_1$ to $C_8$ alkyl and $R^7$ is $OR^4$, $SR^4$, $N(R^4)(R^5)$ or halogen, wherein $R^4$ and $R^5$ are each, independent of the other, hydrogen or substituted or unsubstituted $C_1$ to $C_8$ alkyl;

n is 0, 1 or 2;

provided that when n is 1, A is a protected or an unprotected α-amino acid radical;

when n is 2, A is the same or different protected or unprotected α-amino acid radical; and B is unsubstituted or substituted $C_2$ to $C_8$ alkylene;

and the pharmaceutically acceptable salts thereof.

The compounds of formula I are useful as inhibitors of TNF-α secretion, and particularly useful as inhibitors of the TNF-α converting enzyme (TACE).

The invention also relates to a method for treating a mammal having a condition or a disease characterized by overproduction or unregulated production of TNF-α, comprising administering to the mammal a composition comprising an effective amount of a biologically active compound of formula II:

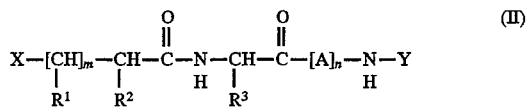

wherein:

X is hydroxamic acid, thiol, phosphoryl or carboxyl;

m is 0, 1 or 2;

$R^1$, $R^2$ and $R^3$ each independent of the other is hydrogen, alkylene(cycloalkyl), $OR^4$, $SR^4$, $N(R^4)(R^5)$, halogen, substituted or unsubstituted $C_1$ to $C_8$ alkyl, $C_1$ to $C_8$ alkylenearyl, aryl, a protected or unprotected side chain of a naturally occurring α-amino acid; or the group —$R^6R^7$, wherein $R^6$ is $C_1$ to $C_8$ alkyl and $R^7$ is $OR^4$, $SR^4$, $N(R^4)(R^5)$ or halogen, wherein $R^4$ and $R^5$ are each, independent of the other, hydrogen or substituted or unsubstituted $C_1$ to $C_8$ alkyl;

n is 0, 1 or 2;

Y is hydrogen, unsubstituted or substituted $C_1$ to $C_8$ alkyl, alkylene(cycloalkyl), the group —$R^8$—$COOR^9$ or the group —$R^{10}N(R^{11})(R^{12})$; wherein $R^8$ is $C_1$ to $C_8$ alkylene; $R^9$ is hydrogen or $C_1$ to $C_8$ alkyl; $R^{10}$ is unsubstituted or substituted $C_1$ to $C_8$ alkylene; and $R^{11}$ and $R^{12}$ are each, independent of the other, hydrogen or $C_1$ to $C_8$ alkyl;

provided that when n is 1, A is a protected or an unprotected α-amino acid radical; and when n is 2, A is the same or different protected or unprotected α-amino acid radical;

and the pharmaceutically acceptable salts thereof;

wherein the compound is capable of reducing serum TNF levels by at least 80% when administered at 25 mg/kg in a murine model of LPS-induced sepsis syndrome;

and a pharmaceutically acceptable carrier.

The invention includes pharmaceutical compositions containing a compound according to formula I as the active component. In addition, pharmaceutical compositions comprising a compound according to formula II and a protein which binds TNF are described. An example of a protein which binds TNF is an anti-TNF antibody or a soluble TNF receptor which is described in EPA 0418014, assigned to the assignee of the instant application. The disclosure of EPA 0418014 is incorporated herein by reference.

The following definitions are used herein. "Alkyl" means a straight or branched, univalent, saturated or unsaturated hydrocarbon group of 1 to 8 carbon atoms. Alkyl groups include the straight-chain groups methyl, ethyl, propyl, butyl, pentyl, hexyl, heptyl, octyl, vinyl, allyl, butenyl, pentenyl, hexenyl, heptenyl and octenyl as well as the branched isomers thereof.

"Substituted alkyl" means an alkyl group substituted with one or more of hydroxy, amino, halogen, or thiol.

"Alkylene" means a bivalent alkyl group as defined above.

"Substituted alkylene" means an alkylene group substituted with one or more of hydroxy, amino, halogen or thiol groups.

"Aryl" means an aromatic or heteroaromatic group, including for example, phenyl, naphthyl, pyridyl, quinolyl, thienyl, furyl and the like, optionally substituted with one or more of $C_1$ to $C_8$ alkyl, hydroxy, amino, halogen, thiol or alkyl groups.

"Alkylene(cycloalkyl)" refers to groups of the structure —$R^{13}$—$R^{14}$ wherein $R^{13}$ is an alkylene as defined above, and $R^{14}$ is a univalent cyclic alkane radical, for example, cyclopropyl, cyclobutyl, cyclopentyl, cyclohexyl, cycloheptyl, and the like.

"Alkylenearyl" means the group —$R^{15}$—$R^{16}$, wherein $R^{15}$ is a substituted or unsubstituted alkylene group as defined above, and $R^{16}$ is a substituted or unsubstituted aryl group as defined above.

"α-Amino acid" refers to any of the 22 common amino acids, e.g., alanine, arginine, asparagine, aspartic acid, cysteine, cystine, glutamine, glutamic acid, glycine, histidine, hydroxyproline, isoleucine, leucine, lysine, methionine, phenylalanine, proline, serine, threonine, tryptophan, tyrosine and valine.

"Protected amino acid" and "protected side chain of an α-amino acid" means the side chains of the amino acid are permanently or temporarily coupled to a chemical group which protects or prevents the side chain from undesired branching, structural modification or rearrangement which can occur during subsequent synthetic steps. Use of such protecting groups for these purposes is well known in the art, as are the protecting groups themselves. Examples of common protecting groups are N-tert-butyloxycarbonyl (Boc) and N-9-fluorenylmethyloxycarbonyl (Fmoc).

"Biologically active" as used in defining certain compounds of formula II, designates a compound capable of (a) inhibiting secretion of TNF-α; (b) preventing cleavage of membrane-bound TNF-α by TACE; or (c) reducing serum TNF levels by at least 80% when administered at 25 mg/kg in a standard murine model of LPS-induced sepsis syndrome.

In the compounds of formulas I and II, preferred radicals for X are hydroxamic acid, thiol and phosphoryl. More preferred X radicals are hydroxamic acid and thiol, while the most preferred radical is hydroxamic acid. The preferred value for m is 1.

Preferred $R^1$ or $R^2$ radicals are hydrogen, $C_1$ to $C_8$ alkyl and $C_1$ to $C_8$ alkylenearyl. Where $R^1$ or $R^2$ is alkyl, preferred is $C_1$ to $C_6$ alkyl and most preferred is $C_1$ to $C_4$ alkyl. Where $R^1$ or $R^2$ is alkylenearyl, preferred alkylene groups are $C_1$ to $C_6$ alkylene, and more preferred is $C_1$ to $C_4$ alkylene; and preferred aryl groups are phenyl and substituted phenyl. The most preferred alkylenearyl group for $R^1$ or $R^2$ is $C_1$ to $C_4$ alkylenephenyl. The most preferred group for $R^1$ is hydrogen and the most preferred group for $R^2$ is isobutyl.

Preferred $R^3$ radicals are substituted and unsubstituted $C_1$ to $C_8$ alkyl and $C_1$ to $C_8$ alkylenearyl. Where $R^3$ is alkyl, preferred is $C_1$ to $C_6$ alkyl and more preferred is $C_1$ to $C_4$ alkyl, with t-butyl being most preferred. Where $R^3$ is $C_1$ to $C_8$ alkylenearyl, preferred alkylene groups are $C_1$ to $C_6$ alkylene, and more preferred is $C_1$ to $C_4$ alkylene; and preferred aryl groups are phenyl, naphthyl, and thienyl, each optionally substituted with hydroxy, amino, halogen, thiol or alkyl groups. Preferred groups for $R^3$ are therefore $C_1$ to $C_4$ alkylenephenyl, $C_1$ to $C_4$ alkylenenaphthyl, and $C_1$ to $C_4$ alkylenethienyl. More preferred is $C_1$ to $C_4$ alkylenenaphthyl, with methylenenaphthyl being most preferred. Where $R^3$ is a protected or unprotected side chain of a naturally occurring α-amino acid, $R^3$ preferably is an arginine, lysine, tryptophan or tyrosine side chain. However, the most preferred radicals for $R^3$ are t-butyl, methylene (cyclohexyl) and methylene-(2'naphthyl).

The radical A is preferably an unprotected naturally-occurring amino acid residue. More preferred naturally-occurring residues are the alanyl radical or an unprotected seryl radical. The most preferred radical for A is an alanyl residue. Further preferred compounds are those where n is 0 or 1, while most preferably n is 1.

Preferred radicals for B are $C_2$ to $C_6$ alkylene. More preferred radicals are $C_2$ to $C_4$ alkylene, with dimethylene being most preferred.

For compounds according to formula II, Y is preferably hydrogen, unsubstituted or substituted $C_1$ to $C_8$ alkyl or the group —$R^{10}N(R^{11})(R^{12})$. Most preferred is the group —$R^{10}N(R^{11})(R^{12})$ with $R^{10}$ preferably being unsubstituted or substituted $C_1$ to $C_6$ alkylene, $R^{11}$ and $R^{12}$ preferably are each independently hydrogen or $C_1$ to $C_6$ alkyl. More preferred $R^{10}$ radicals are unsubstituted or substituted $C_1$ to $C_4$ alkylene, with dimethylene being most preferred. More preferred radicals for $R^{10}$ and $R^{11}$ are hydrogen or $C_1$ to $C_4$ alkyl, with hydrogen being most preferred.

Compounds according to the invention can be prepared utilizing the procedures outlined below, the appended reaction Schemes and the procedures detailed in the Examples below.

General Synthesis

With reference to Scheme 1, the inhibitor compounds may be prepared by converting the carboxylic acid or ester compound (Io), wherein R is H or $C_1$ to $C_8$ alkyl, and P is CBZ, BOC, FMOC or other suitable protective group (Greene T., Wuts P., "Protective Groups in Organic Synthesis", 2nd Ed.; Wiley: New York, 1991; Chapter 7), to the corresponding hydroxamic acid or hydroxamic ester compound (Ip). In compound (Ip), R' is H, TMS, t-Bu, Bzl or other group made by treating these compounds, or an activated form of the carboxylic acid, (Bodanszky, M., Bodanszky, A., "The Practice of Peptide Synthesis"; Springer-Verlag: Berlin, 1984; Chapter II) with a hydroxylamine reagent under conditions which effect the conversion. This is followed by the subsequent removal of the protective group P and R' to generate compound (Iq). The abbreviations used above correspond to the following: Bzl= benzyl; BOC=t-butoxycarbonyl; tBu=t-butyl; CBZ= benzyloxycarbonyl; FMOC=9-fluorenylmethoxycarbonyl; TMS=trimethylsilyl.

A hydroxylamine reagent described above can be hydroxylamine or alternatively, it can be an O-protected hydroxylamine such as commercially available O-trimethylsilyl hydroxylamine, O-tert-butylhydroxylamine, or O-benzylhydroxylamine.

The preparation of precursor compound (Io) may be carried out by condensing the dicarboxylate compound (Ie), with the amine (In), wherein R" is an activating group (Bodanszky, M.; et al., supra.) such as an active ester, anhydride or other group that causes condensation with the amine terminus of compound (In) to occur with formation of a peptide bond.

The preparation of compound (Ie) may be typically carried out as follows: the sodium salt of the 2-oxocarboxylate compound (Ia), is esterified with benzyl bromide to produce the benzyl ester (Ib). Several examples of compound (Ia) are commercially available as various salts or carboxylic acids. Others can be made synthetically (see, for example, Nimitz, J. et al., *J. Org. Chem.* 46:211, 1981; and Weinstock, L. et al., *Synth. Commun.* 11:943, 1981). The benzyl ester compound (Ib) is treated with a Wittig reagent, typically methyl or tert-butyl triphenylphosphoranylidene acetate, to form the alkene (Ic), as a mixture of E- and Z- isomers. Reduction of the alkene compound (Ic) is carried out with hydrogen, in the presence of an appropriate catalyst (typically palladium on activated charcoal), to both hydrogenate the double bond and to remove the benzyl ester, giving the mono-ester compound (Id) as a enantiomeric mixture. Compound (Ie) is obtained by treating the mono-ester compound (Id) using any of a variety of conventional carboxylate activation procedures.

The preparation of the amine compound (In) is achieved by condensing the compound (II) with the amine compound (Ik), wherein P' is an amine protective group other than P, and R" is an activating group such as an active ester, anhydride or other group that causes condensation with the amine terminus of (Ik) to occur with formation of a peptide bond, to give compound (Im). Removal of P' is accomplished under appropriate conditions (Bodanszky, M.; Bodanszky, A., "The Practice of Peptide Synthesis"; Springer-Verlag: Berlin, 1984; Chapter III) to produce compound (In), either as corresponding amine or the amine salt.

Compound (II) is prepared from the commercially available N-protected carboxylic acid, or which can be synthesized by standard methods.

Preparation of (Ik) is carried out by condensing the compound (Ii) with mono-protected diamine (Ih) wherein P is an amine protective group such as CBZ, BOC, FMOC or other suitable protective group; and P' is an amine protective group other than P, and R" is an activating group such as an active ester, anhydride or other group that causes condensation with the unprotected amine terminus of compound (Ih) to occur with formation of a amide bond to give compound (Ij). Removal of P' under appropriate conditions is accomplished to produce compound (Ik), either as the corresponding amine or the amine salt.

Precursor compound (Ih) is prepared in two steps from the amine-nitrile (If). Several examples of compound (If) are available commercially and others can be easily synthesized by classical methods. The amine-nitrile (If) is protected with an appropriate protective group reagent to produce the protected amine-nitrile (Ig). In compound Ig, P is typically CBZ, BOC or FMOC groups, but can be any other suitable group. The protected amine-nitrile (Ig) undergoes reduction with a reagent such as borane-methyl sulfide complex or sodium borohydride/cobalt (II) chloride, to give the mono-protected diamine (Ih) which can be isolated as its amine salt.

Compound (Ii) is prepared from the carboxyl form of the corresponding P'-protected dipeptide or P'-protected amino acid by conventional methods, or can be purchased commercially.

The compounds of formula II may be administered orally, parenterally, via inhalation, transdermally, intra-nasally, intra-ocularlly, mucosally, rectally and topically. Such administration may be in dosage unit formulations containing conventional adjuvants and carrier materials. The term "parenteral" as used herein includes subcutaneous injections, intravenous, intramuscular, intracisternal injection or infusion techniques.

The amount of active ingredient that may be combined with the carrier materials to produce a single dosage form will vary depending upon the host treated and the particular mode of administration. Such carrier materials are well known, and are described, for example, in European Patent Application No. 0 519 748, incorporated herein by reference. It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The following examples are illustrative of the invention. Thin layer chromotagraphy was performed using silica gel 60 $F_{254}$ plates. Reaction schemes for Examples 1 through 9 are appended and follow Example 14. As used herein, "Compound A" refers to the compound N-{D,L-2-(hydroxyaminocarbonyl)methyl-4-methylpentanoyl}L-3-(2'naphthyl)-alanyl-L-alanine amide described by Spatola el. al., Peptides: Chemistry and Biology, Proceedings of the 12th American Peptide Symposium, eds. Smith, J. A., Rivier, J. E., ESCOM, Leiden, Netherlands. Compound A was prepared using the following procedure, and a reaction scheme therefor is appended as reaction scheme A.

Preparation of Compound A

Referring to reaction scheme A and scheme 2, a mixture of 2.0 g (6.3 mmol) of N-BOC-L-3-(2'-naphthyl)alanine and 0.80 g (6.9 mmol) of N-hydroxysuccinimide, and 1.8 g (9.5 mmol) of 1-(3-dimethylaminopropyl)-3-ethylcarbodiimide hydrochloride in anhydrous N,N-dimethylformamide (10 ml) was stirred for 90 minutes at room temperature. To this was added 1.2 g (9.5 mmol) of L-alanine amide hydrochloride, followed by 1.4 ml (9.5 mmol) of triethylamine dissolved in 5 ml of anhydrous N,N-dimethylformamide. After stirring at room temperature for 14 hours, the solvent was removed in vacuo. The residue was dissolved in ethyl acetate (200 ml) and washed with 1M HCl (3×50 ml), water (2×50 ml), saturated sodium bicarbonate (2×50 ml) and finally brine (50 ml). After drying over anhydrous magnesium sulfate, the solution was filtered and concentrated in vacuo to give 2.1 g (86%) yield) of N-BOC-L-3-(2'-naphthyl)alanyl-L-alanine amide ($A_1$) as a white solid. TLC: $R_f$ 0.16 (chloroform-isopropanol 19:1); NMR ($d_6$-DMSO) δ 1.15 (m,3H), 1.24(s,9H), 3.05(m,2H), 4.23 (m,2H), 7.02(s,1H), 7.07(s,2H), 7.35(s,1H), 7.47(m,2H), 7.71(s,1H), 7.82(m,3H), 7.98(d,1H).

A suspension of 1.8 g (4.7 mmol) of ($A_1$) in dichloromethane (15 ml) was cooled with an ice bath. Trifluoroacetic acid (15 ml) was added and the homogeneous solution was stirred at ca. 5° C. for 5 minutes, then allowed to warm to room temperature. After 1 hour the dichloromethane and the trifluoroacetic acid were removed in vacuo. The residue was dissolved in anhydrous N,N-dimethylformamide (18 ml) containing 5.6 ml (33 mmol) of triethylamine. To this was added 1.2 g (4.2 mmol) of (1d) in one portion. After stirring for 14 hours, the N,N-dimethylformamide was removed in vacuo to give a residue. The residue was dissolved in ethyl acetate (250 ml) and washed with 1M HCl (2×75 ml), water (75 ml), saturated sodium bicarbonate solution (2×75 ml) and finally brine (75 ml). After drying over anhydrous magnesium sulfate, the solution was filtered and concentrated to produce 1.5 g (89% yield) of N-{D,L-2-(methoxycarbonyl)methyl-4-methylpentanoyl}-L-3-(2'-naphthyl)alanyl-L-alanine amide ($A_2$) as a white solid. TLC: $R_f$ 0.57 (chloroform-isopropanol 9:1); MS: m/e 455 (M+)

Under an atmosphere of argon, a mixture of 0.62 g (11 mmol) of KOH in 2.8 ml of hot methanol was combined with a mixture of 0.61 g (8.8 mmol) of hydroxylamine hydrochloride in 2.8 ml of hot methanol. After cooling in an ice bath, the reaction was filtered into a flask containing 1.0 g (2.2 mmol) of ($A_2$) and 1 ml of anhydrous N,N-dimethylformamide. After stirring for 18 hours, the solvent was removed in vacuo. The solid was dissolved in hot ethyl acetate (250 ml) and washed with 16 ml of 10% potassium bisulfate solution. The organic phase was heated to its boiling point before drying over anhydrous sodium sulfate. Filtration and subsequent concentration of the filtrate in vacuo produced a solid, which was triturated with ether (50 ml) and collected by filtration to give 0.77 g (77% yield) of N-{D,L-2-(hydroxyaminocarbonyl)methyl-4- methylpentanoyl}-L-3-(2'-naphthyl)alanyl-L-alanine amide (A) as a white solid. The diastereomers of (A) were separated and purified by reverse phase HPLC using a $C_{18}$ column, eluting with water containing 0.1% trifluoroacetic acid with a gradient of acetonitrile (0–60% in 30 minutes) and also containing 0.1% trifluoroacetic acid, ("Method A"), to give a purified early eluting diastereomer and a purified late eluting diastereomer, which had retention times of 21 and 23 minutes respectively. TLC: $R_f$ 0.13 (chloroform-methanol 9:1)

$^1$H NMR($d_6$-DMSO) δ 0.63(d,3H), 0.72(d,3H), 0.90(m, 1H), 1.21(d,3H), 1.26(m,2H) 1.86(m,2H), 2.63(m,1H), 2.99 (m,1H), 3.24(m,1H), 4.18(q,1H), 4.55 (m,1H), 7.05(s,1H), 7.28(s,1H), 7.48(m,3H), 7.72(s,1H), 7.83(m,3H), 7.91(d, 1H), 8.37(d,1H); 13C NMR $^{13}$C NMR ($D_2O/CD_3CN$) δ 17.7, 21.8, 23.1, 26.0, 36.3, 37.4, 41.5, 42.2, 50.1, 55.5, 126.7, 127.1, 128.2, 128.5, 128.8, 129.0, 133.2, 134.2, 135.6, 170.4, 173.0, 177.4, 177.5. MS: m/e 456 (M+)

EXAMPLE 1

Synthesis of N-{D,L-2-(hydroxyaminocarbonyl) methyl-4-methylpentanoyl}-L-3-(2'-naphthyl)alanyl-L-alanine, 2-aminoethyl amide (Compound 1)

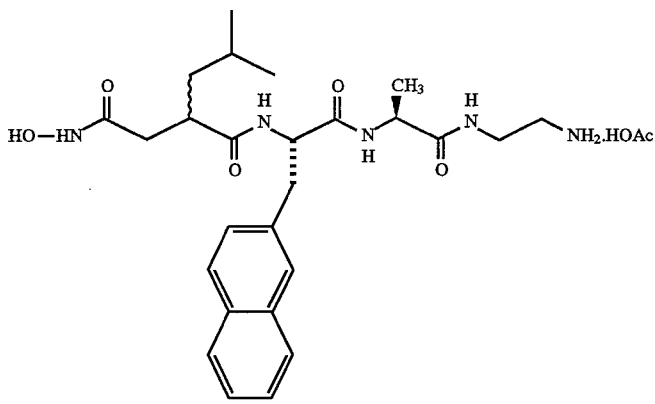

With reference to reaction Scheme 2, a slurry of 25 g (0.164 mol) of the sodium salt of 4-methyl-2-oxopentanoic acid, sodium salt in anhydrous N,N-dimethylformamide (50 ml) containing 19.6 ml (0.164 mol) of benzyl bromide was agitated at room temperature for 4 days. The solvent was removed in vacuo. The residue was dissolved in 250 ml of hexane and washed with water (3×50 ml) and brine (50 ml). After drying over anhydrous magnesium sulfate, the solution was filtered and concentrated in vacuo to give 33.2 g (92% yield) of benzyl 4-methyl-2-oxopentanoate (1a) as a viscous, colorless oil. TLC: $R_f$ 0.70 (ethyl acetatehexane 1:4); $^1$H NMR(CDCl$_3$) δ 0.94(d, 6H), 2.18(m, 1H), 2.71(d, 2H), 5.26(s, 2H), 7.37(m, 5H); $^{13}$C NMR (CDCl$_3$) δ 22.5, 24.2, 48.1, 67.9, 128.7, 128.8, 128.9, 134.7, 161.3, 194.0.

A solution of 26.4 g (0.120 mol) of benzyl ester (1a) and 40.1 g (0.120 mol) of methyl (triphenylphosphoranylidene) acetate in dichloromethane (410 ml) was stirred at room temperature for 18 hours. Removal of the dichloromethane in vacuo produced a solid which was triturated with several volumes of hexane (4×100 ml). The hexane volumes were collected by filtration, combined and concentrated in vacuo to produce an oil which was distilled at reduced pressure (bp.138°–157° C./0.8 mm Hg) to obtain 27.8 g (84% yield) of purified benzyl E,Z-2-isobutyl-3-(methoxycarbonyl) propenoate (1b) as a yellow oil. TLC: $R_f$ 0.53 and 0.67; E and Z isomers (ethyl acetate-hexane 1:4); NMR(CDCl$_3$) δ 0.91(m, 6H, CH(CH$_3$)$_2$), 1.85(m, 1H, CH(CH$_3$)$_2$), 2.23(Z) and 2.79(E) (d, 2H, C=CCH$_2$), 3.62(Z) and 3.74(E) (s, 3H, CO$_2$CH$_3$), 5.23(E) and 5.27(Z) (s, 2H, CO$_2$CH$_2$C$_6$H$_5$), 5.82 (Z) and 6.82(E) (s, 1H, CH=C), 7.35(m, 5H, C$_6$H$_5$).

A suspension of 4.0 g of 10% palladium on activated carbon in a solution of 27.2 g (0.098 mol) of (1b) dissolved in 75 ml of methanol was agitated under 4 atmospheres of hydrogen for 24 hours. Removal of the catalyst by filtration and concentration of the filtrate in vacuo gave an oil which was distilled at reduced pressure (bp.115°–121° C./0.5 mm Hg) to obtain 12.7 g (68%) of D,L-2-isobutyl-3-(methoxycarbonyl)propionic acid (1c) as a colorless oil. $^1$H NMR(CDCl$_3$) δ 0.94 (m, 6H), 1.36(m, 1H), 1.63(m, 2H), 2.58(m, 2H), 2.95(m, 1H), 3.70(s, 3H), 10.8(bs, 1H); $^{13}$C NMR (CDCl$_3$) δ 22.1, 22.3, 25.6, 35.8, 39.2, 40.8, 51.7, 172.2, 181.3.

A solution of 12.3 g (0.065 mol) of (1c) and 7.5 g (0.065 mol) of N-hydroxysuccinimide dissolved in anhydrous tetrahydrofuran (100 ml) was cooled to ca. 5° C. with an ice bath. A solution of 13.5 g (0.065 mol) of 1,3-dicyclohexylcarbodiimide dissolved in anhydrous tetrahydrofuran (50 ml) was added. The mixture was stirred at ca. 5° C. for 1 hour, then allowed to stand overnight under refrigeration. After removal of the dicyclohexylurea by-product by filtration, the filtrate was concentrated in vacuo to produce a solid, which was recrystallized from ethyl acetate-hexane to give 14.5 g (78% yield) of D,L-2-isobutyl-3-(methoxycarbonyl)propionic acid, N-hydroxysuccinimidyl ester (1d) as a white solid. TLC: $R_f$ 0.46 (chloroform-isopropanol 19:1); $^1$H NMR(CDCl$_3$) δ 0.97(m, 6H), 1.61(m,2H), 1.80(m, 1H), 2.72(m, 2H), 2.84(s, 4H), 3.74(s, 3H); $^{13}$C NMR (CDCl$_3$) δ 21.9, 22.5, 25.5, 36.2, 37.2, 41.0, 52.0, 168.8, 170.6, 171.0.

To a solution of 24.9 g (0.10 mol) of benzyl succinimidylcarbonate and 10.2 g (0.11 mol) of aminoacetonitrile hydrochloride dissolved in anhydrous N,N-dimethylformamide (100 ml) was added 15.4 ml (0.11 mol) of triethylamine over a period of 30 minutes at room temperature. The mixture was stirred at room temperature for 12 hours. Removal of the N,N-dimethylformamide in vacuo produced a residue which was dissolved in 350 ml of ethyl acetate. The solution was washed with water (350 ml), 2M HCl (3×50 ml) and brine (50 ml). After drying over anhydrous magnesium sulfate, the solution was filtered and concentrated in vacuo to give 17.3 g (91% yield) of N-CBZ-aminoacetonitrile (1e) as an amber solid. TLC: $R_f$ 0.65 (ethyl acetate-hexane 1:1); $^1$H NMR(CDCl$_3$) δ 4.05(d, 2H), 5.13(s, 2H), 5.46(bt, 1H), 7.35(bs, 5H); $^{13}$C NMR (CDCl$_3$) δ 29.5, 67.9, 116.2, 128.3, 128.5, 128.7, 135.5, 155.7.

Under an atmosphere of dry argon, 24.3 g (0.128 mol) of N-CBZ-aminoacetonitrile (1e) was dissolved in anhydrous tetrahydrofuran (32 ml). The solution was stirred and 64 ml of borane-methylsulfide complex (2M in tetrahydrofuran) was added via syringe. The mixture was heated to reflux and stirred overnight. The mixture was cooled with an ice bath as 5 ml of water was added slowly, with vigorous stirring. The stirring was continued for ca. 5 minutes, then 75 ml of 6M HCl was slowly added. The mixture was stirred for 1 hour, then the excess tetrahydrofuran and dimethyl sulfide was removed in vacuo. The aqueous residue was extracted with ether (2×50 ml). The ether extracts were then discarded. The pH of the aqueous residue was raised to 11 by adding concentrated $NH_4OH$. The resulting aqueous solution was extracted with ethyl acetate (3×100 ml) and the ethyl acetate extracts were combined and washed with brine (50 ml). After drying over anhydrous magnesium sulfate, the solution was filtered and concentrated in vacuo. The resulting oil was dissolved in 30 ml of anhydrous methanol, treated with cold methanolic HCl and concentrated in vacuo to produce a solid. The solid was triturated with ether and collected by filtration to give 15.1 g (51% yield) of N-CBZ-ethylenediamine hydrochloride (1f) as a white powder. $^1$H NMR($D_2O$) δ 3.15(m, 2H), 3.46(m, 2H), 5.14(s, 2H), 7.46 (bs, 5H); $^{13}$C NMR ($D_2O$) δ 41.1, 42.6, 70.4, 131.0, 131.3, 131.7, 132.0, 139.4, 161.7.

A solution of 10.0 g (0.043 mol) of (1f) and 10.3 g (0.036 mol) of N-BOC-L-alanine, N-hydroxysuccinimide ester in anhydrous N,N-dimethylformamide (50 ml) was cooled with an ice bath. To this was added 7.6 ml (0.054 mol) of triethylamine in anhydrous N,N-dimethylformamide (20 ml) over a period of 30 minutes. The reaction was stirred at ca. 5° C. for 1 hour, then at room temperature for 1 hour. The N,N-dimethylformamide was removed in vacuo and the resulting residue was dissolved in 300 ml of ethyl acetate. The solution was washed with 1M HCl (3×100 ml), water (100 ml), saturated sodium bicarbonate solution (3×100 ml) and finally, with brine (100 ml). After drying over anhydrous magnesium sulfate, the solution was filtered and concentrated in vacuo to give 12.4 g (94% yield) of N-BOC-L-alanine, 2-(benzyloxycarbonylamino)ethyl amide (1g) as a white solid. TLC: $R_f$ 0.67 (chloroform-isopropanol 9:1); $^1$H NMR(CDCl$_3$) δ 1.27(d, 3H), 1.40(s, 9H), 3.32(m, 4H), 4.15(m,1H), 5.06(s,2H), 5.51(d,1H), 5.90(m,1H), 7.19(m, 1H), 7.31(bs,5H) $^{13}$C NMR (CDCl$_3$) δ 18.5, 28.2, 39.6, 40.5, 50.1, 66.5, 79.8, 127.9, 128.3, 136.3, 155.4, 156.9, 173.7.

A solution of 12.0 g (0.033 mol) of (1g) in 25 ml of dichloromethane was cooled with an ice bath and 25 ml of trifluoroacetic acid was added. The solution was stirred at ca 5° C. for 20 minutes, then allowed to stir to room temperature. After 90 minutes, the dichloromethane and trifluoroacetic acid were removed in vacuo. The resulting residue was dissolved in 200 ml of ethyl acetate and washed with 2M sodium hydroxide (200 ml) and brine (100 ml). After drying over anhydrous magnesium sulfate, the solution was filtered and concentrated in vacuo to produce 7.86 g (90% yield) of L-alanine, 2-(benzyloxycarbonylamino)ethyl amide (1h) as a white solid. $^1$H NMR(CDCl$_3$) δ 1.28(d, 3H), 2.09(m, 2H), 3.33(m, 4H), 3.47(q, 1H), 5.07(s, 2H), 5.59(bt, 1H), 7.33(bs, 5H), 7.69(bt, 1H);$^{13}$C NMR (CDCl$_3$) δ 21.3, 39.5, 40.9, 50.4, 66.6, 128.0, 128.1, 128.4, 136.4, 156.9, 176.7.

Under an atmosphere of dry argon, a solution of 8.9 g (0.028 mol) of N-BOC-L-3-(2'-naphthyl)alanine and 3.2 ml (0.028 mol) of 4-methylmorpholine in anhydrous N,N-dimethylformamide (20 ml) was cooled to −15° C. and treated with 3.67 ml (0.028 mol) of isobutyl chloroformate. The mixture was stirred at −15° C. for 30 minutes, then a solution of 7.5 g (0.028 mol) of (1h) and 3.2 ml (0.028 mol) of 4-methylmorpholine in anhydrous N,N-dimethylformamide (20 ml) was added slowly, over 10 minutes. The reaction was stirred at −15° C. for 2 hours, then at room temperature for 18 hours. The N,N-dimethylformamide was removed in vacuo and the resulting solid was dissolved in 1 liter of hot ethyl acetate. The hot solution was washed with 1M HCl (3×150 ml), water (150 ml), saturated sodium bicarbonate (3×150 ml) and finally with brine (150 ml). After drying over anhydrous magnesium sulfate, the hot solution was concentrated in vacuo. The resulting yellow solid was triturated with 400 ml of cold 1:3 ethyl acetate-hexane and collected by filtration to give 14.5 g (91% yield) of N-BOC-L-3-(2'-naphthyl)alanyl-L-alanine, 2-(benzyloxycarbonylamino)ethyl amide (1i) as a white solid. TLC: $R_f$ 0.59 (chloroform-isopropanol 9:1); $^1$H NMR (CDCl$_3$) δ 1.26(d, 3H), 1.35(s, 9H), 3.16(m, 6H), 4.42(m, 1H), 4.50(m, 1H), 5.07(s, 2H), 5.25(d, 1H), 5.69(m, 1H), 6.82(m, 1H), 6.90(d, 1H), 7.29(s, 1H), 7.31(bs, 5H), 7.45(m, 2H), 7.61(s, 1H), 7.76(m,3H); $^{13}$C NMR (CDCl$_3$)δ 18.0, 28.2, 38.2, 39.7, 40.6, 49.0, 55.9, 66.6, 80.6, 125.8, 126.2, 127.2, 127.5, 127.6, 127.9, 128.0, 128.4, 132.4, 133.3, 133.8, 134.2, 155.4, 156.7, 171.4, 172.4.

A suspension of 2.5 g (0.0044 mol) of (1i) in dichloromethane (10 ml) was cooled with an ice bath and 10 ml of trifluoroacetic acid was added. The homogeneous solution was stirred at ca. 5° C. for 20 minutes, then allowed to warm to room temperature. After 90 minutes the dichloromethane and trifluoroacetic acid were removed in vacuo. The resulting residue was dissolved in 100 ml of ethyl acetate and washed with 2M NaOH (3×50 ml), water (50 ml) and brine (50 ml). The non-homogeneous solution was transferred to a flask containing 100 ml of absolute ethanol, and heated until it became homogeneous. The hot solution was dried over a small amount of anhydrous sodium sulfate, filtered, and concentrated in vacuo to obtain a solid. The solid was triturated with cold 1:3 ethyl acetate-hexane and collected by filtration to give 1.46 g (71% yield) of L-3-(2'-naphthyl) alanyl-L-alanine, 2-(benzyloxy-carbonyl-amino)ethyl amide (1j) as a white solid. $^1$H NMR(CDCl$_3$) δ 1.33(d, 3H), 1.60(bs, 2H), 2.83(m, 1H), 3.34(m, 5H), 3.82(m, 1H), 4.44 (m, 1H), 5.07(s, 2H), 5.33(t, 1H), 6.92(t, 1H), 7.31(bs, 5H), 7.36(s, 1H), 7.48(m, 2H), 7.65(s, 1H), 7.72(d, 1H), 7.81(m, 3H); $^{13}$C NMR (CDCl$_3$) δ 17.6, 40.6, 40.7, 40.9, 48.6, 56.1, 66.9, 125.4, 125.8, 127.2, 127.4, 127.5, 127.8, 127.9, 128.4, 132.4, 133.4, 135.1, 136.5, 156.1, 172.7, 174.7.

To a solution of 1.4 g (0.003 mol) of (1j) and 0.42 ml (0.003 mol) of triethylamine dissolved in anhydrous N,N-dimethylformamide (2 ml) was added 0.87 g (0.003 mol) of (1d). The mixture was stirred at room temperature for 18 hours. The N,N-dimethylformamide was removed in vacuo. The resulting residue was dissolved in 200 ml of hot ethyl acetate and washed with 1M HCl (3×50 ml), water (50 ml), saturated sodium bicarbonate solution (3×50 ml) and finally brine (50 ml). After drying over anhydrous magnesium sulfate, the hot ethyl acetate solution was filtered and concentrated in vacuo to give 1.7 g (89% yield) of D,L-2-(methoxycarbonyl)methyl-4-methylpentanoyl-L-3-(2'-naphthyl)-alanyl-L-alanine, 2-(benzyloxycarbonylamino) ethyl amide (1k) as an off-white solid. TLC: $R_f$ 0.32 (chloroform-isopropanol 19:1)

Under an atmosphere of argon, a mixture of 2.66 g (0.047 mol) of KOH in 12 ml of hot methanol was combined with a mixture of 2.63 g (0.037 mol) of hydroxylamine hydrochloride in 12 ml of hot methanol. After cooling in an ice bath, the reaction was filtered into a flask containing 6.0 g (0.0095 mol) of (1k) and 12 ml of anhydrous N,N-dimethylformamide. After stirring under argon for 18 hours, the solvent was removed in vacuo. The resulting solid was triturated with 100 ml of ethyl acetate and collected by filtration to give 5.2 g (86% yield) of D,L-2-(hydroxyaminocarbonyl)methyl-4-methylpentanoyl-L-3-(2'-naphthyl)alanyl-L-alanine, 2-(benzyloxycarbonylamino) ethyl amide (1m) as an off white solid. TLC: $R_f$ 0.23 and 0.36 (chloroform-isopropanol 9:1); $^{13}$C NMR($d_6$-DMSO) δ 18.0, 21.7, 23.2, 25.1, 35.7, 36.6, 37.3, 38.7, 40.7, 40.8, 48.5, 54.0, 65.3, 125.3, 125.9, 127.3, 127.4, 127.7, 127.9, 128.3, 131.8, 132.9, 135.7, 136.0, 137.1, 156.1, 167.1, 170.7, 172.7, 174.7. MS: m/e 634 (M+).

A suspension of 1.0 g of 10% palladium on activated carbon in a solution of 2.0 g (0.0031 mol) of (1m) dissolved in glacial acetic acid (75 ml) was agitated under 4 atmospheres of hydrogen for 24 hours. Removal of the catalyst by filtration, and concentration of the filtrate in vacuo produced a residue which was triturated with 50 ml of ether and dried in vacuo to give 2.0 g of crude D,L-2-(hydroxyaminocarbonyl)methyl-4-methylpentanoyl-L-3-(2'-naphthyl)alanyl-L-alanine, 2-(amino)ethyl amide (1).

The diastereomers of (1) were separated by reverse phase FIPLC using a $C_{18}$ column and eluting with water containing 0.1% trifluoroacetic acid with a gradient of acetonitrile (0–60% in 30 minutes) also containing 0.1% trifluoroacetic acid (hereinafter "Method A"). The purified diastereomers (1n) and (1o) had retention times of 20 and 22 minutes, respectively. Diastereomer (1n) showed the following NMR data. $^{13}$C NMR($D_2O$) δ 24.6, 28.9, 29.1, 30.3, 33.2, 43.4, 44.8, 47.0, 48.6, 49.1, 57.6, 62.8, 134.2, 134.6, 135.3, 135.6, 135.8, 135.9, 136.4, 140.2, 141.2, 142.1, 178.3, 180.8, 183.1, 185.4. MS: m/e 500 (M+).

The following is an alternative method, which is a preferred method, for preparing compound 1(c) such that a greater ratio of the desired stereoisomer (R) is produced as compared to the undesired stereoisomer (S). The reaction steps and reference numerals for the respective compounds are shown in Reaction Scheme 10.

By following the procedure of Newman, M. S.; Kutner, A. *J. Am. Chem. Soc.* 1951, 73, 4199, a solution of sodium methoxide was prepared by dissolving 1.29 g (0.056 mol) of sodium in 15 ml of anhydrous methanol, which was added to a slurry of 25 g (0.242 mol) of L-valinol in 500 ml of diethyl carbonate. The reaction mixture was then heated for 2 hours, with 200 ml of distillate collected in the temperature range of 75°–123° C. The distillate was discarded and the reaction mixture was allowed to cool to room temperature and stand overnight. The excess diethyl carbonate was removed from the reaction mixture in vacuo by rotary evaporation to give a residue. The residue was dissolved in 500 ml of ethyl acetate and washed with water (3×200 ml) and brine (200 ml). After drying over anhydrous magnesium sulfate, the solution was filtered and concentrated in vacuo to give a white solid. The solid was recrystallized from ethyl acetate-hexane to produce 23.2 g (74% yield) of (S)-4-isopropyl-2-oxazolidinone 12(a) as white needles. TLC of 12(a): $R_f$ 0.50 (ethyl acetate-hexane 3:1); $^1$H NMR (CDCl$_3$) d 0.90(d, J=6.7 Hz, 3H), 0.97(d, J=6.7 Hz, 3H), 1.72(m, 1H), 3.63(m, 1H), 4.10(dd, J=8.7, 6.4 Hz, 1H), 4.45(m, 1H), 7.32(bs, 1H); $^{13}$C NMR (CDCl$_3$) d 17.5, 17.8, 32.6, 58.3, 68.5, 160.7.

Following the procedure of Vogel, A. In *Vogel's Practical Organic Chemistry*, 4th Ed.; Wiley & Sons: New York, 1978; p 498 and 1208, 4-methylpentanoyl chloride 12(b) was prepared by adding dropwise with stirring, 38 ml (0.52 mol) of thionyl chloride to 50 g (0.43 mol) of 4-methylvaleric acid over 30 minutes. The mixture was heated during the addition, leading to vigorous HCl gas evolution. When the thionyl chloride addition was completed, the reaction mixture was refluxed for 1 hour. The reaction mixture was distilled, with collection of the distillate between 135° and 148° C. The material was re-distilled and 47.3 g (81% yield) of 4-methylvaleroyl chloride 12(b) was collected between 143° and 148° C. as a colorless liquid. $^1$H NMR (CDCl$_3$) d 0.92(d, J=6.2 Hz, 6H), 1.62(m, 3H), 2.90(t, J=7.4 Hz, 2H); $^{13}$C NMR (CDCl$_3$) d 22.0, 27.2, 33.6, 45.3, 173.9.

Following the procedure of Evans, D. A.; Bartroli, J.; Shih, T. L. *J. Am. Chem. Soc.* 1981, 103, 2127, a solution of 32.3 g (0.25 mol) of 12(a) in 500 ml of anhydrous tetrahydrofuran was cooled to –78° C. and 100 ml of 2.5M (0.25 mol) n-butyllithium in hexanes was added. When the addition was complete, the mixture was stirred at –78° C. for 10 minutes, then warmed to 0° C. and stirred for 20 minutes. The reaction mixture was cooled to –78° C. and 34.6 ml (0.25 mol) of 12(b) was added over 10 minutes. Stirring was continued at –78° C. for one hour, then the reaction mixture was allowed to stir at room temperature overnight. The tetrahydrofuran was removed in vacuo by rotary evaporation to produce an orange residue.

The residue was dissolved in 750 ml of ethyl acetate and washed with water (2×250 ml) and brine (3×100 ml). After drying over anhydrous magnesium sulfate, the solution was filtered and concentrated in vacuo to give 60 g of orange oil.

The oil was purified in two batches by flash chromatography on silica gel 60 (500 g). The product was eluted with 1:4 ethyl acetate:hexane to produce 48.6 g (86%) of 12(c) as a pale yellow oil. TLC: $R_f$ 0.42 (1:4 ethyl acetate-hexane) $^1$H NMR (CDCl3) d 0.88(d, J=6.9 Hz, 3H), 0.92(m, 9H), 1.57(m, 3H), 2.37(m, 1H), 2.93(m, 2H), 4.25(m, 2H), 4.44 (m, 1H); $^{13}$C NMR (CDCl$_3$) d 14.5, 17.9, 22.2, 27.6 28.3, 33.2, 33.5, 58.3, 63.2, 153.9, 173.5.

Following the procedure of Evans, D. A.; Ennis, M. D.; Mathre, D. J. *J. Am. Chem. Soc.* 1982, 104, 1737, a mixture of 16.3 ml (0.116 mol) of diisopropylamine and 200 ml of anhydrous tetrahydrofuran was cooled to –5° C. under an atmosphere of dry argon, and 46.5 ml (0.116 mol) of n-butyllithium (2.5M in hexanes) was added. The mixture was stirred at –5° C. for 25 minutes, then cooled to –78° C. A solution of 24.0 g (0.106 mol) of 12(c) in 67 ml of anhydrous tetrahydrofuran was added, and the reaction mixture was stirred at –78° C. for 30 minutes. The reaction was allowed to warm to –5° C. and 27.4 ml (0.317 mol) of allyl bromide was added. The mixture was stirred at –5° C. for 4 hours then 10 ml of water was added, followed by removal of the tetrahydrofuran by rotary evaporation to give an oil. The oil was dissolved in ethyl acetate (500 ml) and washed with water (125 ml) and brine (3×125 ml). After drying over anhydrous magnesium sulfate, the solution was filtered and concentrated in vacuo by rotary evaporation to produce an oil. The oil was purified by filtering it through 100 g of silica gel 60 with 1.25 liters of 1:4 ethyl acetate-hexane. Five fractions of 250 ml each were collected. Each fraction was checked by TLC. The fractions containing purified product were combined and the solvent was removed by rotary, evaporation to give 26.8 g, (95% yield) of 12(d) as a colorless oil. TLC: $R_f$ 0.52 (1:4 ethyl acetate-hexane). $^1$H NMR (CDCl$_3$) d 0.89(m,12H), 1.28(m,1H), 1.53(m,1H), 1.65(m,1H), 2.33(m,3H), 4.06(m,1H) 4.23(m, 2H), 4.46(m,1H), 5.04(m,2H), 5.80(m,1H); $^{13}$C NMR (CDCl$_3$) d 14.5, 18.0, 22.5, 22.8, 26.0, 28.3, 37.5, 40.2, 40.3, 58.5, 62.9, 117.0, 135.1, 153.6, 176.1.

Generally following the methods of Evans, D. A.; Ennis, M. D.; Mathre, D. J. *J. Am. Chem. Soc.* 1982, 104, 1737 a solution of 20.2 g (0.187 mol) of anhydrous benzyl alcohol dissolved in 63 ml of anhydrous tetrahydrofuran was cooled to −5° C. under a dry argon atmosphere and 56.1 ml (0.140 mol) of n-butyllithium (2.5M in hexanes) was added over 10 minutes. The reaction mixture was stirred at −5° C. for 20 minutes, then a solution of 25.0 g (0.0934 mol) of 12(d) dissolved in 380 ml of anhydrous tetrahydrofuran (pre-cooled to −5° C.) was added. The reaction was stirred at −5° C. for 2 hours, then water (50 ml) was added. The reaction was allowed to warm to room temperature. The tetrahydrofuran was removed by rotary evaporation to produce a residue. The residue was dissolved in ethyl acetate (250 ml) and washed with water (125 ml) and brine (125 ml). After drying over anhydrous magnesium sulfate, the solution was filtered and concentrated by rotary evaporation to produce an oil. The oil was purified by flash chromatography on silica gel (240 g). The product was eluted with 97:3 hexane-ethyl acetate to give 38.9 g (85%) of 12(e) as a pale yellow oil. The chiral auxiliary 12(a) was eluted with ethyl acetate for re-use (40% recovery). TLC of 12(e): R$_f$ 0.80 (1:4 ethyl acetate-hexane). $^1$H NMR (CDCl$_3$) d 0.86(d, J=6.8 Hz, 3H), 0.88(d, J=6.8 Hz, 3H), 1.27(m, 1H), 1.57(m, 2H), 2.23(m, 1H), 2.33(m, 1H), 2.58(m, 1H), 5.01(m, 2H), 5.10(s, 2H), 5.71(m, 1H), 7.33(m, 5H); $^{13}$C NMR (CDCl$_3$) d 21.9, 22.9, 26.0, 37.0, 41.0, 43.4, 65.9, 116.7, 128.0, 128.1, 128.4, 135.3, 136.0, 175.5.

By generally following the procedures of Carlsen, P. H. J.; Katsuki, T.; Martin, V. S.; Sharpless, K. B. *J. Org. Chem.* 1981, 46, 3936, a suspension of 38.0 g (0.154 mol) of 12(e) and 145 g (0.679 mol) of sodium periodate in 330 ml of acetonitrile, 330 ml of carbon tetrachloride and 497 ml water was stirred at 0° C., while 0.83 g (2.4 mol %) of ruthenium trichloride hydrate was added. The mixture was stirred at 0° C. for 15 minutes, then allowed to stir to room temperature for 4 hours. The reaction was filtered to remove the solid, using 500 ml of dichloromethane and 250 ml of water to rinse the solid collected. The filtrate was transferred to a separatory funnel and the layers were separated. After drying over anhydrous magnesium sulfate, the lower (dichloromethane) layer was filtered and concentrated in vacuo by rotary evaporation to produce a dark oil. The oil was purified with two successive flash chromatography columns [each column: 500 grams of silica gel 60, eluted with 1900 ml of 1:4 ethyl acetate:hexane, and 1000 ml of ethyl acetate] to produce 26.6 (65% yield) of 12(f) as a viscous oil.

TLC of 12(f): R$_f$ 0.10 (1:4 ethyl acetate-hexane). $^1$H NMR (CDCl$_3$) d 0.88(d, J=6.2 Hz, 3H), 0.92(d, J=6.4 Hz, 3H), 1.33(m, 1H), 1.60(m, 2H), 2.49(dd, J=17.0, 4.8 Hz, 1H), 2.77(dd, J=17.0, 9.5 Hz, 1H), 2.94(m, 1H), 5.15(s, 2H), 7.35(m, 5H), 11.1(bs, 1H); $^{13}$C NMR (CDCl$_3$) d 22.2, 22.4, 25.7, 36.1, 39.2, 41.0, 66.4, 128.0, 128.1, 128.4, 135.8, 174.9, 178.2.

Ethereal diazomethane (Aldrich Chemical Co. *Technical Information Bulletin No. AL-*180) was slowly added to a solution of 22 g (0.083 mol) of 12(f) in 50 ml of diethyl ether until the reaction mixture remained yellow with swirling. The reaction mixture was back titrated to colorlessness with 1:9 acetic acid-diethyl ether. After drying over anhydrous magnesium sulfate the colorless solution was filtered and concentrated in vacuo by rotary evaporation to produce a viscous oil. The oil was dissolved in 100 ml of methanol and transferred to a Parr bottle containing 1.0 g of 10% palladium on charcoal catalyst and shaken under 4 atm. of hydrogen for 6 hours at room temperature. The mixture was filtered through celite and the filtrate was concentrated in vacuo by rotary evaporation to produce an oil. The oil was vacuum distilled to give 13.9 g (89% yield) of 12(f) as a colorless oil; b.p. 110°–123° C./0.2 mmHg.

TLC of 12(f): R$_f$ 0.15 (3:7 ethyl acetate-hexane)

TLC of methyl ester intermediate: R$_f$ 0.73 (3:7 ethylacetate-hexane) TLC of 1(c): R$_f$ 0.23 (3:7 ethyl acetate-hexane). $^1$H NMR of 1(c) (CDCl$_3$) d 0.91(d, J=6.3 Hz, 3H), 0.95(67.4 Hz, 3H), 1.33(m, 1H), 1.64(m, 2H), 2.45(dd, J=16.7, 11.43(bs, 1H); $^{13}$C NMR of 1(c) (CDCl$_3$) d 22.2, 22.4, 25.7, 35.8, 39.3, 40.9, 51.8, 172.3, 181.6.

EXAMPLE 2

Synthesis of N-{D,L-2-(hydroxyaminocarbonyl) methyl-3-methylbutanoyl}-L-3-(2'-naphthyl)-L-alanine amide (Compounds 2 and 3)

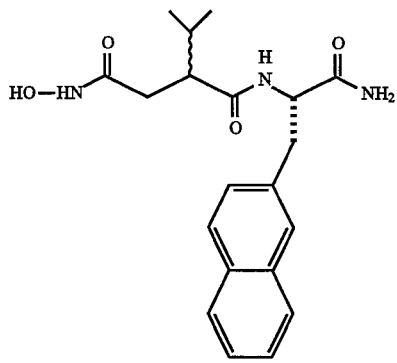

Referring to Scheme 3, Compound (2d) was synthesized from the sodium salt of the 3-methyl-2-oxobutanoic acid by the sequence of reactions used to prepare compound (1d) from 4-methyl-2-oxopentanoic acid, sodium salt.

Compound (2a): 73% yield; bp. 100°–121° C./0.3 mmHg; $^1$H NMR(CDCl$_3$) δ 1.13(d,6H), 3.24(m,1H), 5.27(s,2H), 7.37(m,5H); $^{13}$C NMR(CDCl$_3$) δ 17.0, 37.0, 67.6, 128.4, 128.5, 128.6, 134.5, 161.5, 197.7.

Compound (2b): 58% yield; bp. 125°–147° C./0.6 mmHg; TLC: R$_f$ 0.54(ethyl acetate-hexane 1:4); $^1$H NMR(CDCl$_3$) δ 1.11(d,6H), 2.66(m,1H), 3.62(s, 3H), 5.27(s,2H), 5.79(s, 1H), 7.35(m,5H); $^{13}$C NMR (CDCl$_3$) δ 20.4, 32.7, 51.5, 67.0, 117.0, 128.2, 128.3, 128.5, 135.3, 156.2, 165.4, 168.4.

Compound (2c): 76% yield; bp. 115°–119° C./0.7 mmHg; TLC: R$_f$ 0.09 (ethyl acetatehexane 1:4); $^1$H NMR(CDCl$_3$) δ 0.96(d,3H), 0.99(d,3H), 2.09(m, 1H), 2.43(m, 1H), 2.76(m, 3H), 3.69(s,3H); $^{13}$C NMR(CDCl$_3$) δ 19.1, 19.8, 29.7, 32.1, 47.0, 51.7, 172.8, 180.4.

Compound (2d): 55% yield; TLC: R$_f$ 0.60(chloroform-isopropanol 19:1); $^1$H NMR(CDCl$_3$) δ 1.06(d,3H), 1.08(d, 3H), 2.12(m, 1H), 2.58(m,1H), 2.84(m,5H), 3.07(m, 1H), 3.72(s,3H); $^{13}$C NMR(CDCl$_3$) δ 19.4, 19.6, 25.6, 30.3, 33.1, 45.2, 52.1, 168.9, 169.6, 171.5.

The diastereomers (2) and (3) can be made from L-3-(2'-naphthyl)alanine amide hydrochloride (8b) and compound (2d), using the sequence of reactions used to prepare Compound (1) from Compounds (1j) and (1d). Compounds (2) and (3) were separated by reverse phase HPLC as described above.

Compound (2): HPLC retention time (Method A) 21 minutes. $^1$H NMR(CD$_3$CN/D$_2$O) δ 0.19(d,3H), 0.50(d,3H), 1.38(m, 1H), 2.24(m,3H), 2.95(m,1H), 3.50(m,1H), 4.68(m, 1H), 7.48(m,3H), 7.76(s,1H), 7.83(m,3H); $^{13}$C NMR (CD$_3$CN/D$_2$O) δ 20.2, 20.3, 31.1, 33.4, 38.0, 50.2, 55.5, 126.7, 127.2, 128.4, 128.6, 129.1, 129.2, 133.8, 134.4, 136.6, 171.5, 176.3, 176.4. MS: m/e 371 (M+).

Compound (3): HPLC retention time (Method A) 23.1 minutes. MS: m/e 371 (MH+).

EXAMPLE 3

Synthesis of N-[3-(hydroxyaminocarbonyl) propanoyl]-L-3-(2'-naphthyl)alanyl-L-alanine amide (Compound 4)

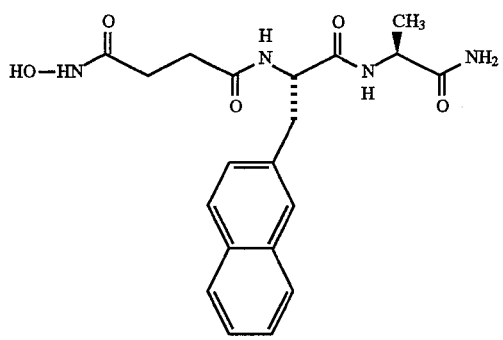

Referring to Scheme 4, to a solution of 1.74 g (10 mmol) of tert-butyl hydrogen succinate (Buchi, G.; Roberts, C. J. Org Chem., 33:460, 1968) and 1.15 g (10 mmol) of N-hydroxy-succinimide in anhydrous tetrahydrofuran (20 ml) was added 2.06 g (10 mmol) of 1,3-dicyclohexylcarbodiimide. After stirring at room temperature overnight, the reaction was filtered to remove the dicyclohexylurea by-product. The filtrate was concentrated in vacuo to give a residue. Chromatography on silica gel using ethyl acetate-hexane (1:1), provided 2.3 g (84% yield) of tert-butyl succinimidyl succinate (4a) as a white solid. TLC: R$_f$ 0.50 (ethyl acetate-hexane 1:1); NMR(d$_6$-DMSO) δ 1.39(s,9H), 2.56(m,2H), 2.80(bs,4H), 2.86 (m,2H).

A solution of 0.70 g (1.8 mmol) of (A$_1$) dissolved in 5.0 ml of trifluoroacetic acid was stirred at room temperature for 90 minutes. The trifluoroacetic acid was removed in vacuo to give a residue which was triturated with ether (20 ml) and dried in vacuo to give 0.72 g of a pink solid. A portion (0.35 g) of the solid was dissolved in 2.0 ml of anhydrous N,N-dimethylformamide. To this was added 0.24 g (0.87 mmol) of (4a) and 0.18 ml (1.3 mmol) of triethylamine. After stirring at room temperature for 2 hours, the solvent was removed in vacuo to produce a residue. Chromatography on silica gel using chloroform-isopropanol 9:1 provided 0.32 g (84% yield) of N-[3-(tert-butoxycarbonyl)propanoyl]-L-3-(2'-naphthyl)alanyl-L-alanine amide (4b) as white solid. TLC: R$_f$ 0.33 (chloroform-isopropanol 9:1); $^1$H NMR (d$_6$-DMSO) δ 1.23(d,3H), 1.30(s,9H), 2.27(m,4H), 2.93(m, 1H), 3.20(m, 1H), 4.22(m,1H), 4.61(m,1H), 7.03(s,1H), 7.22(s,1H), 7.46(m,3H), 7.75(s,1h), 7.83(m,3H), 8.07(d, 1H), 8.19(d, 1H); $^{13}$C NMR(d$_6$-DMSO) δ 18.3, 27.8, 30.1, 30.3, 37.6, 48.1, 54.1, 79.6, 125.4, 126.0, 127.4, 127.5, 127.9, 131.9, 133.0, 135.8, 170.8, 171.1, 171.6, 174.1.

A solution of 0.29 g (0.64 mmol) of (4b) dissolved in 10 ml of trifluoroacetic acid was stirred at room temperature for 30 minutes. The trifluoroacetic acid was removed in vacuo to give a residue which was triturated with ether (20 ml) and dried in vacuo to give 0.24 g (95% yield) of N-[3-carboxypropanoyl]-L-3-(2'-naphthyl)alanyl-L-alanine amide (4c) as a white solid. TLC: R$_f$ 0.04 (chloroform-isopropanol 9:1); $^1$H NMR(d$_6$-DMSO) δ 1.23(d,3H), 2.29 (m,4H), 2.92(m,1H), 3.21(m,1H), 4.21(m,1H), 4.58(m,1H), 7.04(s,1H), 7.23(s,1H), 7.46(m,3H), 7.75(s,1H), 7.83(m, 3H), 8.06(d,1H), 8.21(d,1H); $^{13}$C NMR (d$_6$-DMSO) δ 18.3, 29.1, 30.0, 37.6, 48.2, 54.1, 125.4, 126.0, 127.4, 127.5, 128.0, 131.9, 133.0, 135.8, 170.8, 171.3, 173.9, 174.1.

Under an atmosphere of dry argon, a solution of 0.22 g (0.56 mmol) of (4c) and 0.062 ml (0.56 mmol) of 4-methylmorpholine anhydrous N,N-dimethylformamide (2 ml) was cooled to −15° C. and treated with 0.073 ml (0.56 mmol) of isobutyl chloroformate. The mixture was stirred at −15° C. for 15 minutes, then a solution of 0.10 g (0.81 mmol) of (O-benzyl)hydroxylamine in anhydrous N,N-dimethylformamide (0.5 ml) was added. The mixture was stirred at −15° C. for 1 hour, then at room temperature for 1 hour. The solvent was removed in vacuo. The resulting solid was triturated with ethyl acetate and collected by filtration to obtain 0.20 g (73% yield) of N-[3-(benzyloxyaminocarbonyl)propanoyl]-L-3-(2'-naphthyl)alanyl-L-alanine amide (4d) as a white solid. TLC: R$_f$ 0.46 (chloroform-isopropanol 8:2); $^1$H NMR (d$_6$-DMSO) δ 1.26 (d,3H), 2.25(m,4H), 2.95(m,1H), 3.22 (m,1H), 4.23(m,1H), 4.57(m,1H), 4.74(s,2H), 7.03(s,1H), 7.16(s,1H), 7.36(bs, 5H), 7.46(m,3H), 7.77(s,1H), 7.83(m,3H), 8.12(d,1H), 8.32 (d,1H), 11.03(s,1H); $^{13}$C NMR(d$_6$-DMSO) δ 18.3, 27.9, 30.4, 37.6, 48.4, 54.5, 77.0, 125.6, 126.1, 127.6, 128.1, 128.4, 128.5, 129.0, 132.0, 133.2, 136.0, 136.2, 169.0, 171.0, 171.7, 174.3.

A suspension of 0.20 g of 5% palladium on activated carbon in a solution of 0.10 g (0.20 mmol) of (4d) in 4 ml of glacial acetic acid was agitated under 4 atmospheres of hydrogen for 18 hours. Removal of the catalyst by filtration, and concentration of the filtrate in vacuo produced a residue which was triturated with 10 ml of ether and dried in vacuo to give a solid. Chromatography on Baker octadecyl reverse phase gel, eluting with water-acetonitrile-acetic acid (57:40:3), provided 0.065 g (79% yield) of N-[3-(hydroxyaminocarbonyl)-propanoyl]-L-3-(2'-naphthyl)alanyl-L-alanine amide (4), as a white solid. TLC: R$_f$ 0.05 (chloroform-isopropanol 8:2); $^1$H NMR(d$_6$-DMSO) ε 1.24 (d,3H), 2.08(m,2H), 2.28(m,2H), 2.92(m,1H), 3.22(m,1H0, 4.20(q,1H), 4.54(m,1H), 7.02(s,1H), 7.20(s,1H), 7.46(m, 3H), 7.76(s,1H), 7.84(m,3H), 8.12(d,1H), 8.27(m,1H), 10.39(s,1H); $^{13}$C NMR(d$_6$-DMSO) δ 18.0, 27.6, 30.4, 37.3, 47.9, 54.0, 125.3, 125.8, 127.2, 127.3, 127.7, 131.7, 132.8, 135.7, 168.3, 170.5, 171.3, 174.0.

EXAMPLE 4

Synthesis of N$_α$-{D,L-2-(hydroxyaminocarbonyl) methyl-4-methylpentanoyl}-L-arginyl-L-alanine, 2-aminoethyl amide (Compound 5)

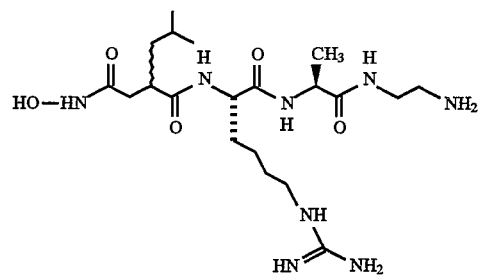

With reference to Scheme 5, Compound (5a) was synthesized from Compound (1h) and N$_α$-BOC-N$_g$-(di-CBZ)-L-arginine in 79% yield, by following the method used to prepare Compound (1i). TLC: $R_f$ 0.59 (chloroform-isopropanol 9:1); $^1$H NMR (CDCl$_3$) δ 1.18(d,3H), 1.40(s, 9H), 1.62(m,4H), 3.27(m,4H), 3.89(m,2H), 4.09(m,1H), 4.21(m,1H), 5.06(s,2H), 5.13(m,2H), 5.22(s,2H), 5.58(m, 1H), 5.67(m,1H), 6.70(d,1H), 6.80(m,1H), 7.33(bm,15H), 9.30(m,1H), 9.42(m, 1H); $^{13}$C NMR (CDCl$_3$) δ 17.3, 25.0, 27.9, 28.3, 39.8, 40.7, 44.0, 49.3, 54.7, 66.6, 67.1, 69.0, 80.4, 127.9, 128.0, 128.3, 128.4, 128.5, 128.8, 128.9, 134.5, 136.6, 155.7, 156.9, 160.7, 163.5, 172.2, 172.4.

Compound (5b) was prepared from Compound (5a) in 87% yield, by the method used to prepare Compound (1j). TLC: $R_f$ 0.11 (chloroform-isopropanol 9:1); $^1$H NMR (CDCl$_3$) δ 1.28(d,3H), 1.43(m,1H), 1.70(m,4H), 3.30(m, 6H), 3.91(m,2H) 4.34(m,1H), 5.03(s,2H), 5.11(s,2H), 5.22 (s,2H), 5.50(m,1H), 7.01(m,1H), 7.33(bm,15H), 7.76(d,1H), 9.25(m,1H), 9.41(m,1H); $^{13}$C NMR (CDCl$_3$) δ 17.7, 24.5, 31.1, 40.3, 40.6, 44.1, 48.6, 54.1, 66.7, 66.9, 68.9, 127.9, 128.0, 128.1, 128.2, 128.3, 128.4, 128.5, 128.8, 134.6, 136.3, 136.8, 155.7, 157.1, 160.4, 163.7, 172.8, 175.4.

Compound (5c) was prepared from Compounds (5b) and (1d) in 88% yield, as a mixture of diastereomers, with the method used to prepare Compound (1k). $^1$H NMR (d$_6$-DMSO; mixture of diastereomers) δ 0.79(bm,6H), 1.06(m, 1H), 1.13 & 1.20(d, 3H), 1.52(bm,6H), 2.40(m, 1H), 2.71 (m,1H), 3.03(bm,5H), 3.47 & 3.54(s,3H), 3.88(m, 2H), 4.18(m,2H), 5.00(s,2H), 5.04(s,2H), 5.24(s,2H), 7.35(bm, 18H), 7.59 & 7.71(d,1H), 7.66 & 7.94(t,1H), 8.13 & 8.45 (d,1H); $^{13}$C NMR(d$_6$-DMSO); mixture of diastereomers) δ 17.8 & 18.3, 21.8 & 22.2, 22.9 & 23.0, 25.0 & 25.2, 25.4, 28.4 & 28.7, 36.4 & 36.5, 39.6, 40.0, 41.2 & 41.3, 44.3 & 44.4, 48.1 & 48.2, 51.1 & 51.4, 52.4 & 53.1, 65.3, 66.1, 68.2, 127.5, 127.6, 128.3, 128.6, 135.2, 135.3, 137.0, 155.0, 156.1, 156.2, 159.5, 162.8, 162.9, 170.9, 171.0, 171.9, 172.0, 172.8, 174.0, 174.8.

Hydroxamate (5d) was prepared from Compound (5c) in 78% yield as a mixture of diastereomers.

Hydroxamate (5d) was deprotected by hydrogenolysis to give Compound (5) in 59% yield as a mixture of diastereomers. HPLC retention times (method A) 10.1 and 10.3 minutes; $^1$H NMR(D$_2$O; mixture of diastereomers) δ 0.89 (m,6H), 1.25(m,1H), 1.39(m,3H), 1.69(bm,6H), 2.38(m, 2H), 2.85(m,1H), 3.15(dd,2H), 3.22(dd,2H), 3.53(m,2H), 4.32(m, 2H); $^{13}$C NMR (D$_2$O; mixture of diastereomers) δ 24.3 & 24.5, 28.9 & 29.1, 30.4 & 30.5, 32.4 & 32.6, 33.4 & 33.5, 35.7 & 35.8, 43.4 & 43.6, 44.9, 47.0 & 47.1, 48.4 & 48.5, 49.0 & 49.1, 49.2, 57.8 & 58.0, 61.1 & 61.4, 164.8, 178.4 & 178.5, 181.4 & 181.8, 183.5 & 183.8, 185.6 & 186.4. MS: m/e 459(M+).

EXAMPLE 5

Synthesis of N$_\alpha$-{D,L-2-(hydroxyaminocarbonyl) methyl-4-methylpentanoyl}L-lysinyl-L-alanine amide (Compound 6)

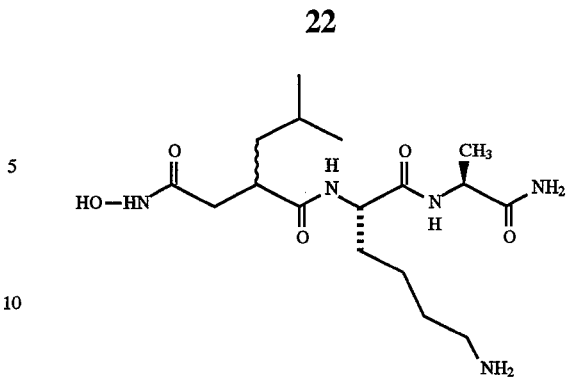

Referring to Scheme 6, a solution of 5.0 g (0.010 mol) of Nα-BOC-Nε-CBZ-L-lysine p-nitrophenyl ester and 1.5 g (0.012 mol) of L-alanine amide hydrochloride and 1.67 ml (0.012 mol) of triethylamine in anhydrous N,N-dimethylformamide (50 ml) was stirred at room temperature for 16 hours before the solvent was removed in vacuo. The resulting residue was dissolved in ethyl acetate (200 ml) and washed with 3M NaOH (3×100 ml), water (3×100 ml), 1M HCl (2×100 ml) and finally with brine (100 ml). After drying over anhydrous sodium sulfate, the solution was filtered and concentrated in vacuo to give 4.3 g (96% yield) of Nα-BOC-Nε-CBZ-L-lysyl-L-alanine amide (6a) as a white solid. TLC: $R_f$ 0.32 (chloroform-isopropanol 9:1); $^1$H NMR (d$_6$-DMSO) δ 1.20(d,3H), 1.35(bm, 6H), 1.37(s,9H), 2.97(m, 2H), 3.86(m,1H), 4.21(m,1H), 5.00(s,2H), 6.95(d,1H), 7.06 (s, 1H), 7.24(t,1H), 7.34(m,6H), 7.78(d,1H); $^{13}$C NMR (d$_6$-DMSO) δ 18.6, 22.8, 28.2, 29.2, 31.4, 40.1, 47.8, 54.5, 65.2, 78.2, 127.8, 128.4, 137.3, 155.5, 156.1, 171.7, 174.2.

Compound (6b) was prepared from Compounds (6a) and (1d) in 69% yield using the method previously described to prepare Compound (A$_2$). TLC: $R_f$ 0.21 and 0.29 (chloroform-isopropanol 9:1); $^1$H NMR (d$_6$-DMSO; mixture of diastereomers) δ 0.81(m,3H), 0.88(m,3H), 1.17 & 1.23 (d,3H), 1.40(bm,8H), 2.46(m,3H), 2.78(m,1H), 2.98(m,2H), 3.54 & 3.56(s,3H), 4.08(m,1H), 4.16(m,1H), 5.00(s,2H), 7.04(m,1H), 7.23(t,1H), 7.34(m,6H), 7.58 & 7.68(d,1H), 8.10 & 8.42(d,1H).

Compound (6c) was prepared from Compound (6b) in 48% yield, using the method previously described to prepare (A$_3$). TLC: $R_f$ 0.16 (chloroform-isopropanol 8:2). MS: m/e 522 (M+).

The diastereomers (6A) and (6B) were prepared from Compound (6c) by the method used to prepare Compound (1) from Compound (1m). HPLC purification (method A) produced an early-eluting isomer (6A) and a late-eluting isomer (6B).

Compound (6A): HPLC retention time (method A): 9.2 minutes; $^1$H NMR (d$_6$-DMSO) δ 0.81(d,3H), 0.88(d,3H), 1.06(m,1H), 1.28(d,3H), 1.40(bm,7H), 1.75(m,1H), 2.03(m, 1H), 2.22(m,1H), 2.73(m,3H), 4.01(m,1H), 4.13(m,1H), 7.04(s,1H), 7.11(s,1H), 7.78(bs,3H), 8.06(d,1H), 8.48(d, 1H), 10.61(s,1H); $^{13}$C NMR(d$_6$-DMSO) δ 17.6, 21.8, 22.4, 23.5, 25.5, 26.4, 30.1, 35.7, 39.2, 40.0, 41.3, 48.4, 53.1, 168.1, 171.4, 174.8, 175.5; MS: m/e 387 (M+).

Compound (6B): HPLC retention time (method A): 9.9 minutes; $^1$H NMR(d$_6$-DMSO) δ 0.81(d,3H), 0.87(d,3H), 1.08(m,1H), 1.18(d,3H), 1.46(bm,7H), 1.68(m,1H), 2.05(m, 1H), 2.17(m,1H), 2.76(m,3H), 4.16(m,2H), 7.04(s,1H), 7.35 (s,1H), 7.67(d,1H), 7.73(bs,3H), 8.08(d,1H), 10.58(s,1H); $^{13}$C NMR(d$_6$-DMSO) δ 18.5, 22.1, 22.2, 23.2, 25.1, 26.3, 30.5, 35.5, 39.2, 40.1, 41.3, 47.8, 52.0, 167.9, 171.1, 174.0, 174.3; MS: m/e 387 (MH+).

EXAMPLE 6

Synthesis of N-{D,L-2-(hydroxyaminocarbonyl) methyl-4-methylpentanoyl}L-tyrosyl-L-alanine amide (Compound 7)

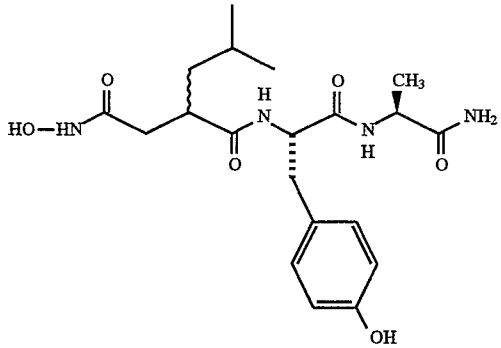

With reference to Scheme 7, Compound (7a) was prepared from N-BOC-(O-benzyl)-L-tyrosine p-nitrophenyl ester and L-alanine amide hydrochloride in 99% yield, with the method used to prepare Compound (6a). TLC: $R_f$ 0.51 (chloroform-isopropanol 9:1); $^1$H NMR ($d_6$-DMSO) δ 1.22 (d,3H), 1.30(s,9H), 2.67(m,1H), 2.91(m,1H), 4.09(m,1H), 4.22(m,1H), 5.05(s,2H), 6.90(m,3H), 7.06(s,1H), 7.18(m, 2H), 7.28(s,1H), 2.38(bm,5H), 7.88(d,1H); $^{13}$C NMR ($d_6$-DMSO) δ 18.5, 28.1, 36.4, 47.8, 56.0, 69.1, 78.1, 114.3, 127.5, 127.7, 128.3, 130.1, 130.2, 137.2, 155.2, 156.8, 171.2, 174.0.

Compound (7b) was prepared from Compound (7a) as a mixture of diastereomers in 64% yield with the method used to synthesize Compound (6b). TLC: $R_f$ 0.53 and 0.57 (chloroform-isopropanol 9:1); $^1$H NMR ($d_6$-DMSO; mixture of diastereomers) δ 0.60 & 0.68(d,3H), 0.76 & 0.82(d,3H), 1.04(m,1H), 1.19 & 1.26(d,3H), 1.40(m,2H), 2.31(bm, 2H), 2.68(m,2H), 3.05(m,1H), 3.48 & 3.55(s,3H), 4.20(m,1H), 4.44(m,1H), 5.03 & 5.04(s,2H), 6.87(m,2H), 7.06(bs,1H), 7.15(m,3H), 7.38(bm,5H), 7.69 & 7.78(d,1H), 8.15 & 8.39 (d, 1H); $^{13}$C NMR ($d_6$-DMSO; mixture of diastereomers) δ 18.0 & 18.4, 21.9 & 22.1, 22.9 & 23.1, 24.6 & 25.1, 35.8 & 36.0, 36.4 & 36.6, 39.4 & 39.7, 41.1 & 41.2, 47.9 & 48.0, 51.2 & 51.4, 53.9 & 54.6, 69.1 & 69.2, 114.2 & 114.3, 127.5, 127.7, 128.4, 130.1, 130.2, 137.2, 156.8 & 156.9, 170.6 & 170.8, 171.9 & 172.7, 173.8 & 173.9, 174.0 & 174.4.

Compound (7c) was prepared from Compound (7b) in 48% yield with the method used to prepare Compound (6c). A single diastereomer of Compound (7c) was isolated by HPLC (method A). $^1$H NMR (CD$_3$OD). δ 0.46(m,6H), 0.61(m,1H), 0.76(m,1H), 1.13(m,1H), 1.28(d,3H), 1.89(m, 1H), 2.17(m,1H), 2.45(m,2H), 3.10(m,1H), 4.18(m,1H), 4.39(m,1H), 4.83(s,2H), 6.70(m,2H), 6.97(m,2H), 7.17(m, 5H); $^{13}$C NMR(CD$_3$OD) δ 17.8, 22.2, 23.9, 26.3, 36.8, 37.2, 42.2, 43.0, 50.8, 56.7, 71.0, 115.9, 128.5, 128.9, 129.5, 131.1, 138.8, 159.1, 170.9, 173.8, 178.2, 178.6.

The diastereomer (7c) was deprotected under 4 atmospheres of hydrogen in the presence of 10% palladium on carbon in methanol to produce Compound (7) in 92% yield.

EXAMPLE 7

Synthesis of N-{D,L-2-(hydroxyaminocarbonyl) methyl-4-methylpentanoyl}-L-3-(2'-naphthyl)alanine amide (Compounds 8 and 9)

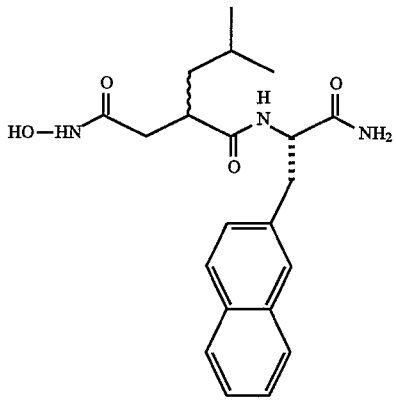

With reference to Scheme 3, a solution of 3.2 g (0.010 mol) of N-BOC-L-3-(2'-naphthyl)alanine and 1.3 g (0.011 mol) of N-hydroxysuccinimide dissolved in 10 ml of anhydrous tetrahydrofuran was cooled to ca. 5° C. A solution of 2.3 g (0.011 mol) of 1,3-dicyclohexylcarbodiimide dissolved in 5 ml of anhydrous tetrahydrofuran was added, and the mixture was stirred at ca. 5° C. for 30 minutes, then at room temperature for 30 minutes. The dicyclohexylurea by-product was removed by filtration, and the filtrate was transferred to a flask containing 1.5 ml (0.022 mol) of concentrated NH$_4$OH. After the mixture had stirred at room temperature for 1 hour, the solvent was removed in vacuo to give a residue. The residue was dissolved in ethyl acetate (350 ml) and washed with water (100 ml), 1M HCL (100 ml), water (100 ml), saturated sodium bicarbonate solution (100 ml) and finally with brine (100 ml). After drying over anhydrous magnesium sulfate, the solution was filtered and concentrated in vacuo to produce a solid. The solid was recrystallized from ethyl acetate to give 2.2 g (70% yield) of N-BOC-L-3-(2'-naphthyl)alanine amide (8a) as a white solid. TLC: $R_f$ 0.50 (chloroform-isopropanol 9:1); $^1$H NMR ($d_6$-DMSO) δ 1.27(s,9H), 2.92(m,1H), 3.12(m, 1H), 4.22(m, 1H), 6.91(d,1H), 7.07(s,1H), 7.44(s,1H), 7.50(m,3H), 7.75 (s,1H), 7.85(m,3H); $^{13}$C NMR ($d_6$-DMSO) δ 28.3, 37.9, 55.7, 78.1, 125.5, 126.1, 127.5, 127.6, 128.0, 132.0, 133.1, 136.2, 155.4, 173.7.

A stream of hydrogen chloride gas was bubbled into a solution of 1.95 g (0.0062 mol) of N-BOC-L-3-(2'-naphthyl) alanine dissolved in 60 ml of anhydrous 1,4-dioxane, for 15 minutes. Ether (400 ml) was added, causing a solid to precipitate. The solid was collected by filtration and dried in vacuo to give 1.36 g (88% yield) of L-3-(2'-naphthyl)alanine amide hydrochloride (8b). $^1$H NMR($d_6$-DMSO) δ 3.27(m, 2H), 4.10(m,1H), 7.48(m,3H), 7.55(s,1H), 7.79(s,1H), 7.86 (m,3H), 8.14(s,1H), 8.40(bm,3H); $^{13}$C NMR($d_6$-DMSO) δ 37.0, 53.6, 125.9, 126.3, 127.7, 127.9, 128.1, 128.4, 132.4, 133.0, 133.1, 169.8.

The diastereomers (8) and (9) can be made from L-3-(2'-naphthyl)alanine amide hydrochloride (8b) and (1d), using the sequence of reactions used to prepare Compound (1) from Compounds (1j) and (1d).

Compound (8): HPLC retention time (method A) 22.6 minutes. $^1$H NMR (CD$_3$CN/D$_2$O) δ 0.71(m,6H), 1.09(m, 2H), 1.28(m,1H), 2.12(m,2H), 2.59(m,1H), 2.84(m,1H), 3.11(m,1H), 4.45(m,1H), 6.94(m,7H). MS: m/e 385 (M+).

Compound (9): HPLC retention time (method A) 24.3 minutes, MS: m/e 385 (M+).

EXAMPLE 8

Synthesis of N-{D,L-2-(hydroxyaminocarbonyl)methyl-4-methylpentanoyl}-L-3-(2'-naphthyl-alanyl-L-serine amide (Compound 10).

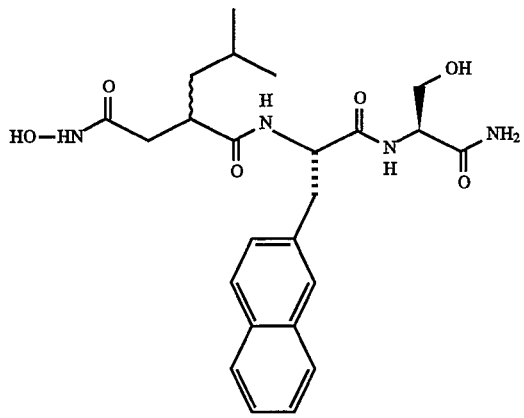

With reference to Scheme 8, N-BOC-L-3-(2'-naphthyl)alanyl-L-(O-benzyl)serine amide (10a) was prepared from N-BOC-L-3-(2'-naphthyl)alanine and L-(O-benzyl)serine amide in 80% yield with the method used to prepare (7a). TLC: $R_f$ 0.51 (chloroform-isopropanol 9:1); $^1$H NMR ($d_6$-DMSO) δ 1.24(s,9H), 2.93(m,1H), 3.19(m,1H), 3.65(m,2H), 4.34(m,1H), 4.48(m,1H), 4.51(s,2H), 7.16(d,1H), 7.27(s,1H), 7.34(m,5H), 7.46(m,4H), 7.78(s,1H), 7.82(m,3H), 8.04 (d,1H); $^{13}$C NMR ($d_6$-DMSO) δ 28.0, 37.4, 52.5, 55.9, 70.0, 72.1, 78.2, 125.4, 125.9, 127.3, 127.4, 127.5, 127.8, 128.2, 131.8, 32.9, 135.9, 138.2, 155.4, 171.3, 171.5.

L-3-(2'-naphthyl)alanyl-L-(O-benzyl)serine amide (10b) was prepared from Compound (10a) in 95% yield with the method used to prepare Compound (1j). TLC: $R_f$ 0.08 (chloroform-isopropanol 9:1); $^1$H NMR $d_6$-DMSO) δ 2.81 (m,1H), 3.15(m,1H), 3.42(m,3H), 3.63(m,2H), 4.37(s,2H), 4.43(m,1H), 7.32(m,6H), 7.46(m,4H), 7.72(s,1H), 7.82(m,3H), 8.14(d,1H); $^{13}$C NMR ($d_6$-DMSO) δ 40.6, 52.0, 55.8, 70.0, 72.0, 125.3, 125.9, 127.4, 127.5, 127.7, 128.0, 128.2, 131.8, 133.0, 136.2, 138.1, 171.5, 174.0.

Compound (10c) was prepared from Compounds (10b) and (1d) as a mixture of diastereomers in 97% yield following the method used to prepare Compound (1k). TLC: $R_f$ 0.69 and 0.73 (chloroform-isopropanol 9:1); $^1$H NMR ($d_6$-DMSO; mixture of diastereomers) δ 0.25 & 0.40(d,3H), 0.68 & 0.79(d,3H), 1.00(m,1H), 1.32(m,2H), 2.31(bm,3H), 2.64 (m,1H), 2.98(m,1H), 3.37 & 3.50(s,3H), 3.68(m,2H), 4.48 (m,1H), 4.49 & 4.53(s,2H), 4.72(m,1H), 7.35(bm,6H), 7.44 (m,4H), 7.78(m,4H), 7.93 & 7.99(d,1H), 8.30 & 8.49(d,1H); $^{13}$C NMR ($d_6$-DMSO; mixture of diastereomers) δ 21.4 & 22.1, 22.8, 24.5 & 25.1, 36.3 & 36.6, 37.1, 39.6, 41.0 & 41.1, 51.1 & 51.4, 52.6 & 52.7, 53.7 & 54.2, 69.8 & 69.9, 72.1, 125.3, 125.8, 127.4, 127.5, 127.6, 127.8, 128.2, 131.8 & 131.9, 132.9 & 133.0, 135.7 & 135.8, 138.1, 170.0, 171.2, 171.3, 171.8, 172.5, 174.0, 174.2.

Compound (10d) was prepared from Compound (10c) in 74% yield with the method used to prepare Compound (1m). TLC: $R_f$ 0.12 (chloroform-isopropanol 9:1).

Compound (10) was prepared from Compound (10d) in 84% yield with the method used to prepare Compound (1n). HPLC retention times: 25.2 and 27.1 minutes (method A). MS: m/e 472 (M+).

EXAMPLE 9

Synthesis of N-{D,L-2-(hydroxyaminocarbonyl)methyl-4-methylpentanoyl}L-3-(2'-naphthyl)-alanyl-L-alanine methylamide (Compound 11)

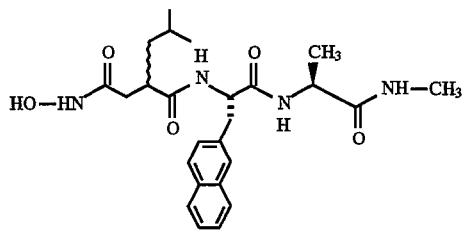

Referring to Scheme 9, Compound (11a) was prepared from N-BOC-L-3-(2'-naphthyl)alanine and L-alanine methylamide hydrochloride, in 89% yield using the method previously described to prepare Compound (1i). TLC: $R_f$ 0.58 (chloroform-isopropanol 9:1); $^1$H NMR ($d_6$-DMSO) δ 1.21(d,3H), 1.25(s,9H), 2.54(d,3H), 2.91(m,1H), 3.18(m, 1H), 4.28(m,2H), 7.04(d,1H), 7.46(m,3H), 7.75(s,1H), 7.83 (m,4H), 8.07(d,1H); $^{13}$C NMR ($d_6$-DMSO) δ 18.5, 25.5, 28.0, 37.5, 48.1, 55.7, 78.1, 125.4, 125.9, 127.3, 127.4, 127.5, 127.9, 131.8, 132.9, 135.9, 155.3, 171.1, 172.3.

Compound (11b) was prepared from Compounds (11a) and (1d), in 86% yield using the method previously described to prepare Compound ($A_2$). TLC: $R_f$ 0.57 and 0.62 (chloroform-isopropanol 9:1);

$^1$H NMR ($d_6$-DMSO; mixture of diastereomers) δ 0.23 & 0.40(d,3H), 0.70 & 0.79(d,3H), 1.01(m,2H), 1.18 & 1.26(d, 3H), 1.32(m,2H), 2.22(m,2H), 2.53(d,3H), 2.92(m,1H), 3.22 (m,1H), 3.38 & 3.39(s,3H), 4.22(m,1H), 4.63(m,1H), 7.44 (m,4H), 7.73(s,1H), 7.81(m,4H), 8.22 & 8.46(d,1H).

Compound (11) was prepared from Compound (11b) in 23% yield using the method previously described to prepare Compound ($A_3$). TLC: $R_f$ 0.18 (chloroform-isopropanol 9:1).

EXAMPLE 10

Synthesis of N-{D,L-2-(hydroxyaminocarbonyl)methyl-4-methylpentanoyl}-L-3-amino-2-dimethylbutanoyl-L-alanine 2-aminoethylamide (Compound 13)

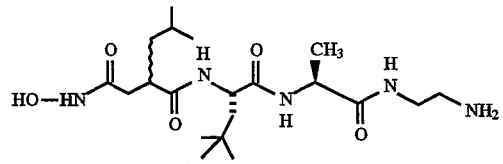

Following Reaction Scheme 10, N-Boc-L-tert-leucine 13(b) was prepared by treating L-tert-leucine (Aldrich Chemical) with di-tert-butyl dicarbonate and diisopropylethyl amine in dimethylfluoride (DMF). Then (13b) was treated with NHS and dicyclohexylcarbodiimide (DCC) in anhydrous tertrahydrofuran to produce N-Boc-L-tert-leucine N-hydroxysuccinimidyl ester, which then is coupled with (1h) from Reaction Scheme 2 and Example 1to produce (13c). Compound (13) was prepared from (13c) by following procedures similar to those described in Example 1 and shown in Reaction Scheme 2 for the synthesis of compound (1).

$^1$H NMR ($d_6$-DMSO) δ 0.76(d, J=5.6 Hz, 3H), 0.82(d, J=6.1 Hz, 3H), 0.90(s,9H), 1.06(m,1H), 1.17(d, J=6.6 Hz, 3H), 1.39(m,2H), 2.08(m,2H), 2.69(m,2H), 2.86(m, 1H), 3.18(m,2H), 4.19(m,2H), 8.30(m,1H), 8.03(d, J=7.0 Hz,

1H), 7.86(d, J=8.9 Hz, 1H), $^{13}$C NMR (d$_6$-DMSO) δ 18.4, 22.6, 23.5, 25.7, 27.1, 34.5, 36.2, 39.2, 40.0, 41.1, 48.8, 60.3, 167.8, 170.1, 172.6, 174.5.

EXAMPLE 11

Inhibition of TNF-α Release by T-cells

The following example demonstrates the selective in vitro inhibition of T-cell TNF-α secretion, as compared to TNF-β and IFN-γ secretion, by Compound 1.

Human peripheral blood T-cells were purified from peripheral blood mononuclear cells by rosetting with 2-aminoethylisothiouronium bromide hydrobromide-treated sheep erythrocytes. After hypotonic lysis of sheep erythrocytes, monocytes were depleted by plastic adherence for one hour at 37° C. The peripheral big T-cells were stimulated with anti-CD3 antibody (OKT3) which was immobilized on the culture wells at 10 μg/ml in PBS plus 10 mg/ml of the phorbol ester, PMA. Culture medium comprised RPMI 1640 medium containing 10% fetal bovine serum, 50 U/ml penicillin, and 50 μg/ml streptomycin. The stimulation was performed in the presence or absence of the inhibitor Compound 1 (200 μM), and TNF-α in the medium was assayed by ELISA. Results are shown in Table I.

TABLE I

Effect of Compound 1 on Cytokine Production by Peripheral Blood T Cells

|  | 3 Hrs. | 24 Hrs. | 48 Hrs. |
|---|---|---|---|
| TNF-α (pg/ml) |  |  |  |
| with Compound 1 | † | 100 | 300 |
| without Compound 1 | 100 | 325 | 800 |
| TNF-β (pg/ml) |  |  |  |
| with Compound 1 | † | 160 | 1050 |
| without Compound 1 | † | 160 | 830 |
| IFN-γ (ELISA OD) |  |  |  |
| with Compound 1 | 0.2 | 0.9 | 1.08 |
| without Compound 1 | 0.3 | 0.65 | 1.15 |

† undetectable

After 3 hours, there was 100 pg/ml of TNF-α in the medium of cells without Compound 1 and no detectable TNF-α in the medium of cells with 200 μM of Compound 1. At 24 and 48 hours, Compound 1 inhibited TNF-α release by 72% and 63%, respectively, while there was no inhibitory effect on the release of TNF-β or interferon-γ. Compound 1 clearly demonstrates selective inhibition of TNF-α secretion and has no effect on either TNF-β or interferon-γ secretion.

EXAMPLE 12

Compound 1 Induced Increase in Cell Surface TNF-α on PMA+Ionomycin-Stimulated Human T-cells This example describes the effects of Compound 1 on cell surface TNF-α for human T-cells which have been stimulated by PMA and ionomycin.

The alloreactive human T-cell clone, PL-1, does not express cell surface TNF-α in the absence of stimulation. However, after stimulation with PMA plus ionomycin, cell surface TNF-α, as well as the ligands for CD40 and 41BB, are rapidly induced on the cell surface. Detection of cell surface TNF-α was performed by staining with an Fc fusion protein consisting of an Fc portion of a human IgG1 molecule (IgGFc) coupled with an extracellular domain of TNF receptor (p80). Detection of cell surface ligands for 41BB and CD40 was performed by staining with analogous Fc fusion proteins consisting of IgGFc and extracellular domains of 41BB and CD40, respectively. A fusion molecule consisting of IgGFc and the extracellular portion of the IL-4 receptor (IL-4R:Fc) was utilized as a negative control for staining, since PL-1 cells do not express cell-surface IL-4 in response to PMA stimulation. TNFR:Fc and IL-4R:Fc fusion proteins are described in EP 0 464 533, incorporated herein by reference. The same general procedures used to construct the TNFR:Fc and IL-4R:Fc fusion molecules were utilized in the construction of the 41BB:Fc and CD40:Fc molecules. Fc fusion proteins bound to their respective cell-surface ligands were then detected with a biotinylated anti-human IgG1 followed by streptavidin-phycoerythrin. The intensity of staining was measured by a FACS (fluorescence activated cell sorting) scan flow cytometer. The results are shown in Table II.

TABLE II

Effects of Compound 1 on Expression of Cell Surface TNF-α, IL-4, 41BBL and CD40L on PMA and Ionomycin-Stimulated Human T-Cells (MFI, arbitrary units)

|  | TNF-α | 41BBL | CD40L | IL-4 |
|---|---|---|---|---|
| No stimulation | 10 | 10 | 10 | 10 |
| 4h after stimulation |  |  |  |  |
| + Compound 1 | 3040 | 344 | 107 | 10 |
| − Compound 1 | 83 | 428 | 107 | 10 |
| 18h after stimulation |  |  |  |  |
| + Compound 1 | 616 | 9 | 46 | 10 |
| − Compound 1 | 7 | 5 | 19 | 10 |

The specificity of Compound 1 for increasing cell surface TNF-α is apparent. Cells stimulated with PMA and ionomycin for four hours in the presence of Compound 1, followed by staining with TNFR:Fc as described above, displayed a MFI of 3040 as compared to 83 in the absence of Compound 1. The effect of Compound 1 was specific for TNFR:Fc binding as no increase on 41BB:Fc or CD40:Fc binding was detected. A substantial increase in cell-surface TNF-α resulted in a 100-fold increase in TNFR:Fc binding in the presence of Compound 1 (MFI was 616) as compared to an MH of 7 in absence of Compound 1, after 18 hours of stimulation. Under the same conditions, 41BB:Fc and CD40:Fc binding were enhanced only approximately 2-fold.

EXAMPLE 13

In vivo Inhibition of TACE

500 μg Compound A Versus Compound 1 Versus Control

Female Balb/c mice (18–20 g) were injected i.v. with 400 μg of LPS. Simultaneously, the mice were injected subcutaneously with 500 μg of Compound A or Compound 1 in 0.5 ml of saline containing 0.02% DMSO. Control mice received LPS intravenously and saline/DMSO subcutaneously. Two hours following the LPS injection, serum was obtained and pooled from two mice in each treatment group. TNF-α levels were determined by ELISA and are shown in the following Table III.

TABLE III

| Comparison of 500 μg Each of Compound 1 versus Compound A on LPS-Induced Serum TNF Levels in Balb/c Mice (pg/ml) | | | |
|---|---|---|---|
| | Compound 1 | Compound A | Saline/DMSO |
| Serum TNF-α level | undetectable | 65 | 157 |

Compound 1 inhibits the secretion of TNF-α at least by 80%, and essentially by 100%, as the TNF-α levels were undetectable. Comparatively, Compound A reduced serum TNF-α levels by approximately 60% as compared to the saline/DMSO control.

In a similar manner to the procedure described above, mice were injected i.v. with 400 μg LPS. Simultaneously, the mice were injected subcutaneously with 500 μg Compound 1 in 0.5 ml saline containing 0.02% DMSO. Two hours later, serum was obtained and pooled. TNF-α levels were determined by ELISA. Results are shown in Table IV in pg/ml.

TABLE IV

| Effect of 500 μg Compound 1 on LPS-Induced Serum TNF Levels in Balb/c Mice (pg/ml) | | | |
|---|---|---|---|
| Experiment No. | LPS + Cpmd 1 | LPS only | LPS + Saline |
| 1 | 301 | 1696 | 1268 |
| 2 | 269 | 2527 | 1768 |
| 3 | 281 | 1833 | 1732 |

In experiment 1, Compound 1 reduced serum TNF-α levels by 82% as compared to TNF-α levels in mice that received LPS only. As compared to mice that received LPS+saline, Compound 1 reduced serum TNF-α levels by 76%. In experiment 2, Compound 1 reduced serum TNF-α levels by 89% as compared to TNF-α levels in mice that received LPS only. As compared to mice that received LPS+saline, Compound 1 reduced serum TNF-α levels by 85%. In experiment 3, Compound 1 reduced serum TNF-α levels by 85% as compared to TNF-α levels in mice that received LPS only. As compared to mice that received LPS+saline, Compound 1 reduced serum TNF-α levels by 84%. Overall, Compound 1 reduced serum TNF-α levels by 85.4±2.98% as compared to TNF-α levels in mice that received LPS only. From Tables III and IV, Compound 1 effectively reduces serum TNF-α levels by at least 80% when administered at 25 mg/kg in a murine model of LPS-induced sepsis syndrome.

250 μg Compound A Versus Compound 1 Versus Control

Female Balb/c mice (18–20 g) were injected i.v. with 450 μg of LPS. Simultaneously, the mice were injected subcutaneously with 250 μg of Compound A or Compound 1 in 0.25 ml of saline containing 0.02% DMSO. Control mice received LPS intravenously and saline/DMSO subcutaneously. Two hours following the LPS injection, serum was obtained from three mice in each treatment group. TNF-α levels were determined by ELISA. The results are expressed as the mean optical density (OD) obtained in the ELISA from each treatment group, and are shown in Table V. The background OD of the control sample was 0.162±0.003.

TABLE V

| Comparison of 250 μg Each of Compound 1 versus Compound A on LPS-Induced Serum TNF Levels in Balb/c Mice | | | |
|---|---|---|---|
| LPS + Saline | LPS + Saline + DMSO | Cmpd 1 + DMSO | Cmpd A + DMSO |
| 0.271 ± 0.022 | 0.268 ± 0.040 | 0.147 ± 0.004 | 0.299 ± 0.023 |

Table V illustrates the effect of Compound 1 and Compound A on inhibiting serum TNF-α release in LPS-stimulated mice. Compound 1 reduced serum TNF-α levels, to those of the control, thereby indicating a complete inhibition of TNF-α secretion at 250 μg/ml. Compound A had no effect in reducing serum TNF-α levels as shown by the similarity in OD readings between LPS+Saline, LPS+Saline+DMSO, and Compound A.

EXAMPLE 14

Serum Stability of Compound A and Compound 1

Each of Compound 1 and Compound A was diluted to 50 μM in normal mouse serum and incubated at 37° C. At various times, aliquots were withdrawn, diluted 100-fold into ice-cold PBS, and tested for inhibitory, efficacy against purified TACE. After 40 minutes, Compound A showed a decrease in inhibitory effect corresponding to a 3–4 fold loss in concentration of the compound, and Compound 1 showed no decrease in inhibitory, effect.

SCHEME 1

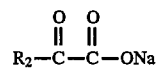

(Ia)

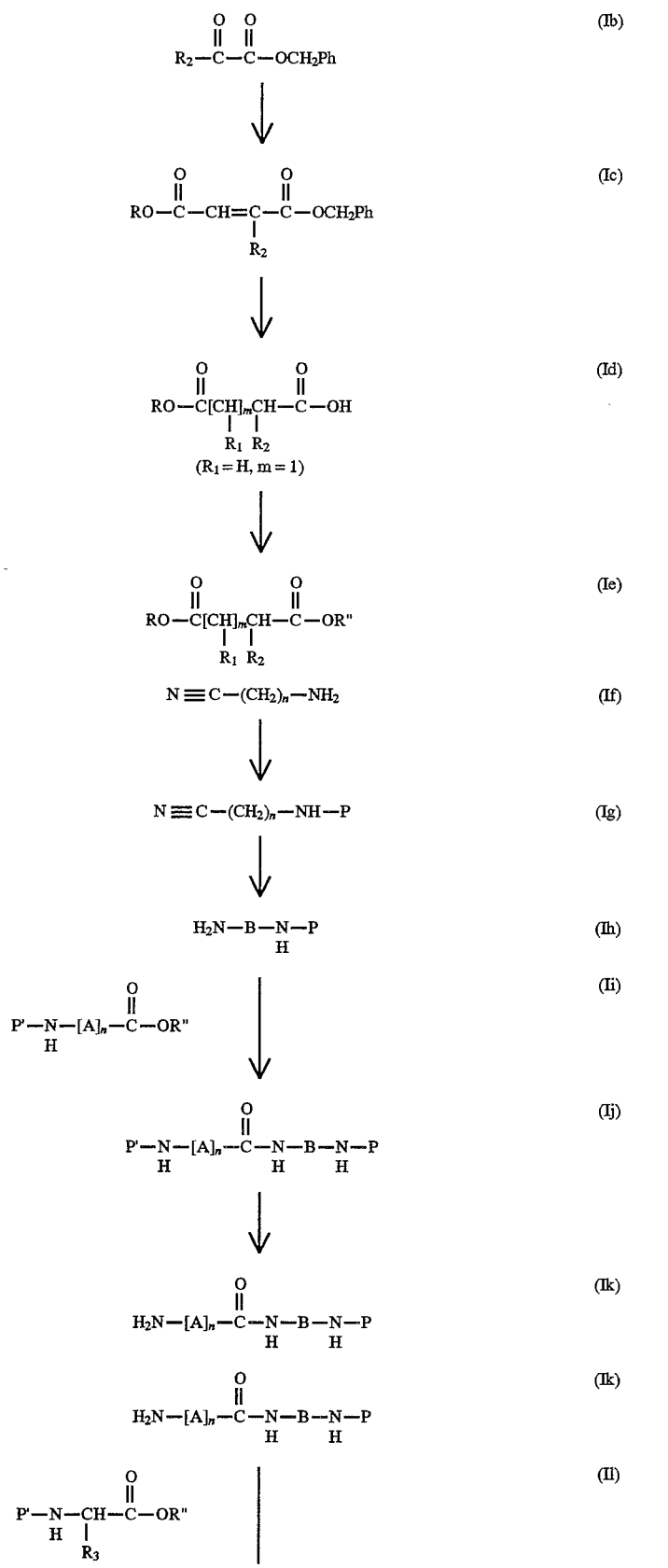

SCHEME A
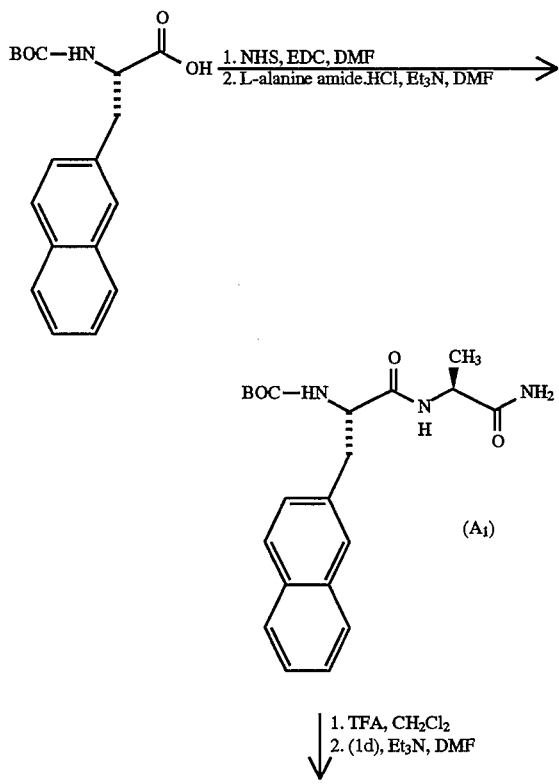
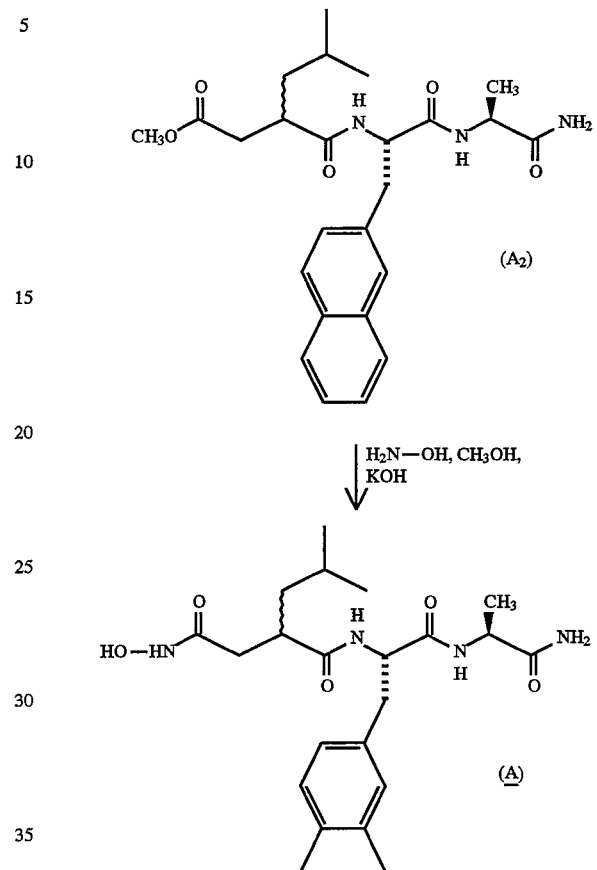
SCHEME 2
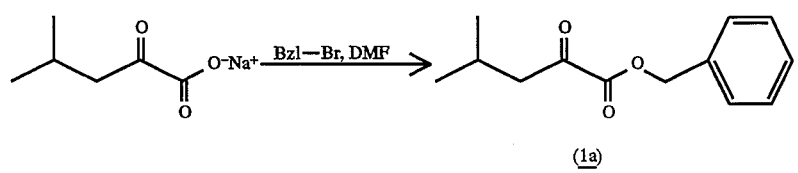

SCHEME 5
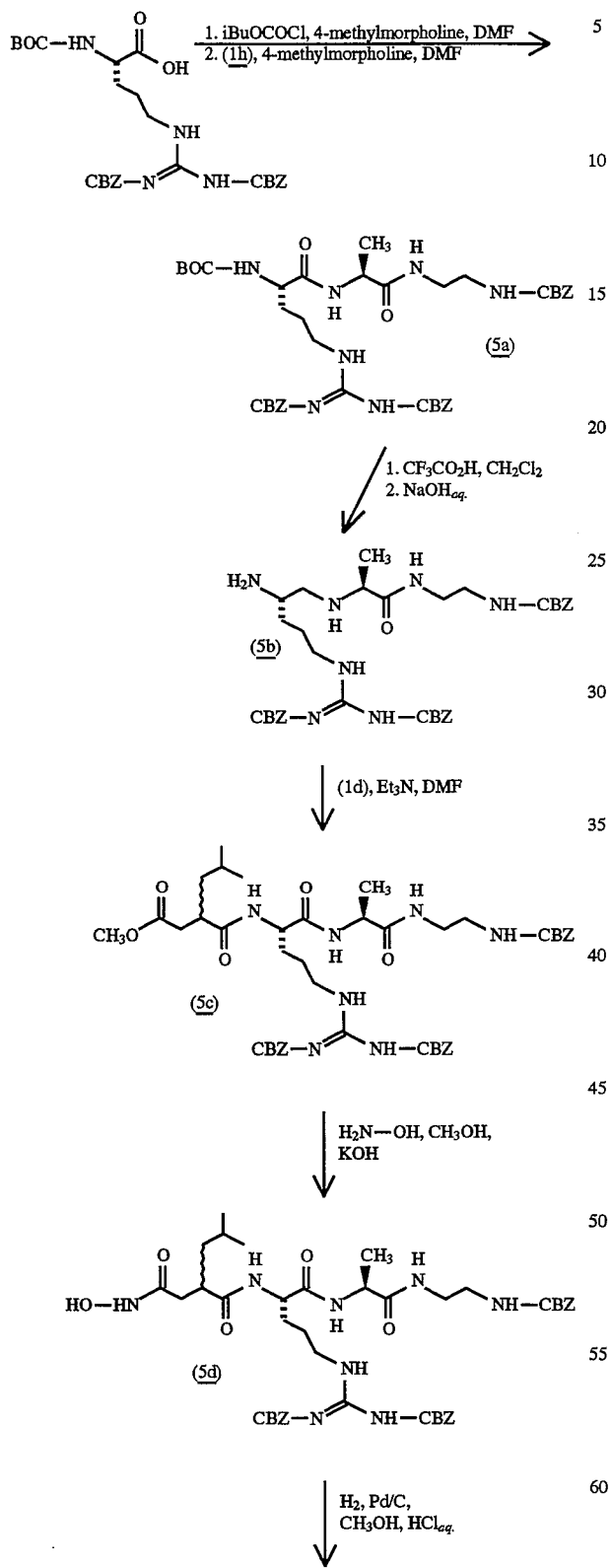
SCHEME 5 -continued
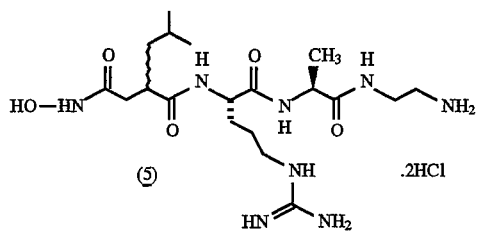
SCHEME 6
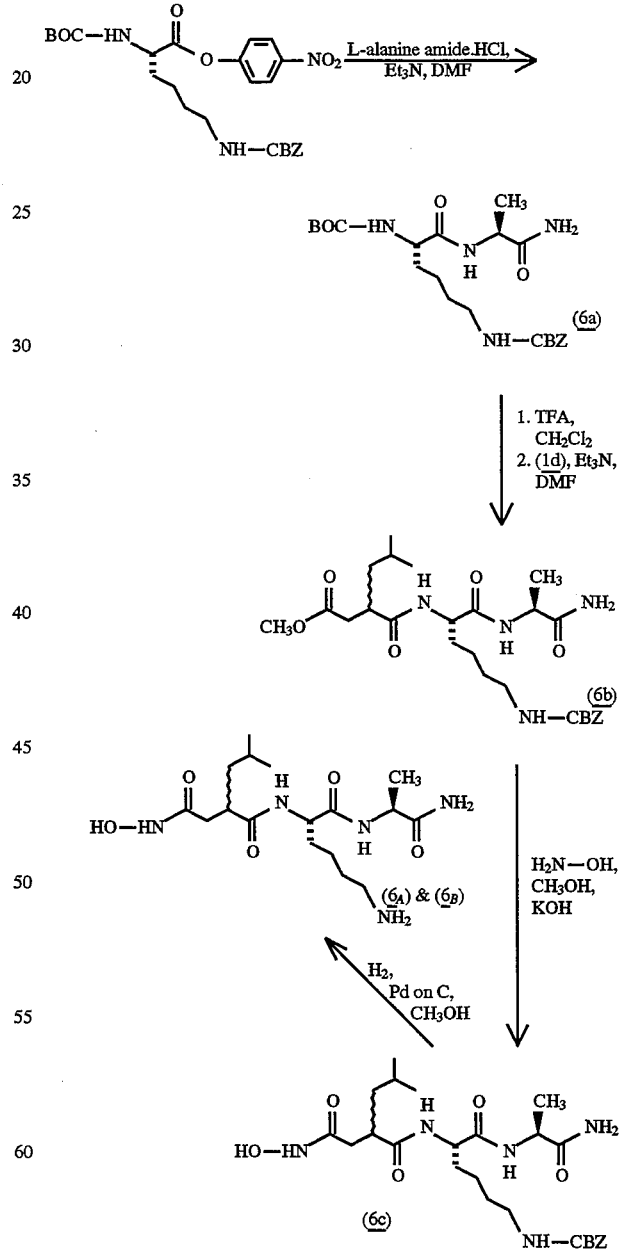

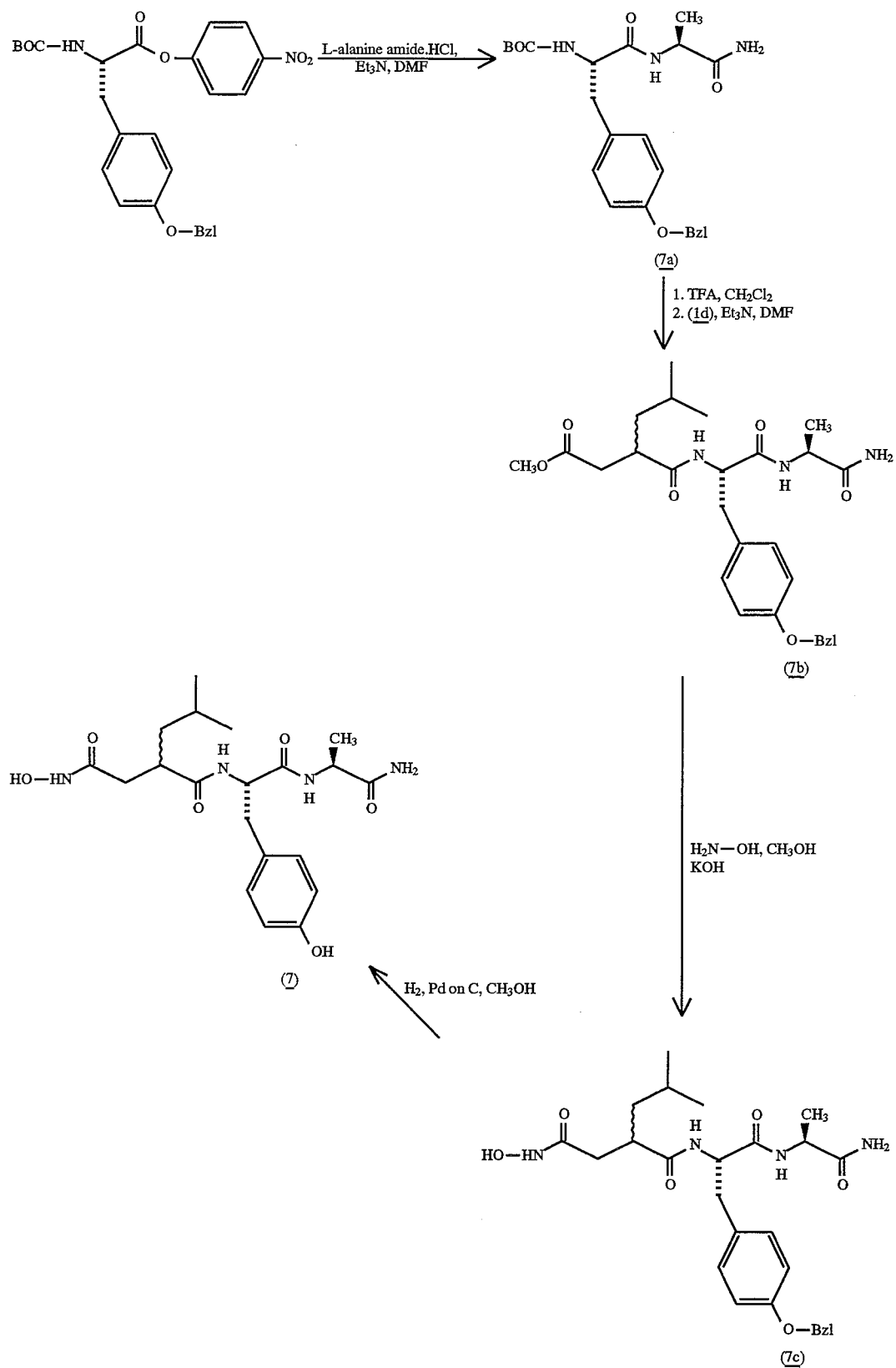

SCHEME 8
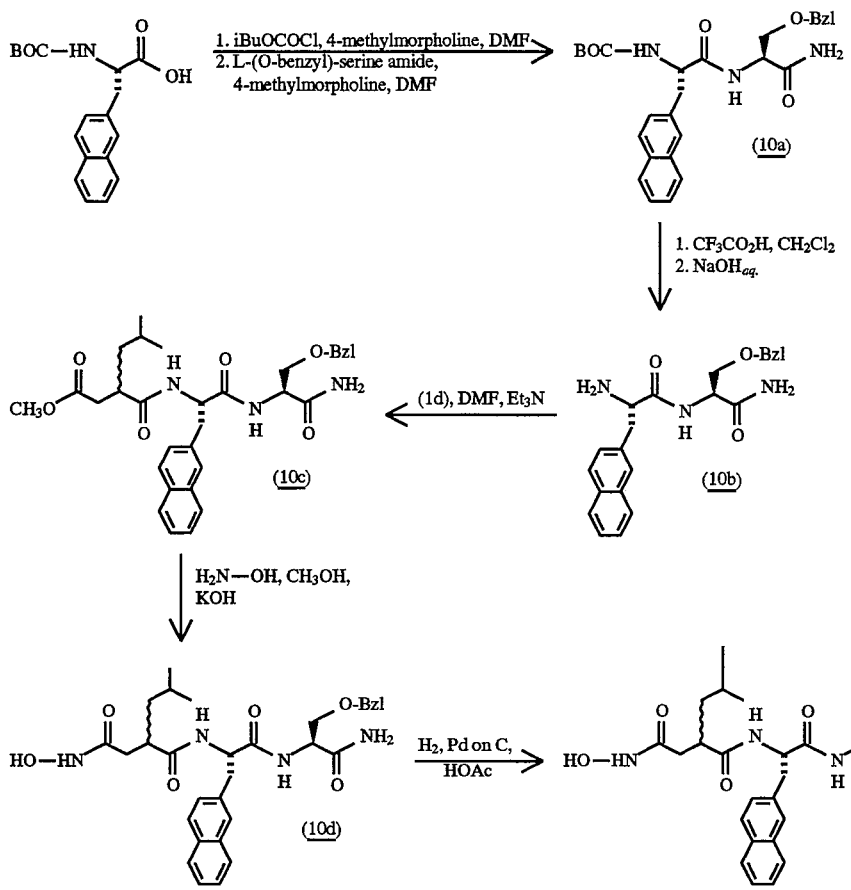
SCHEME 9
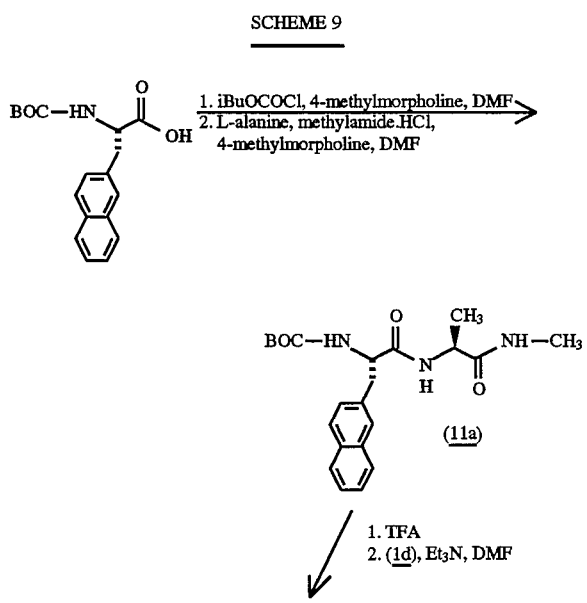
-continued
SCHEME 9
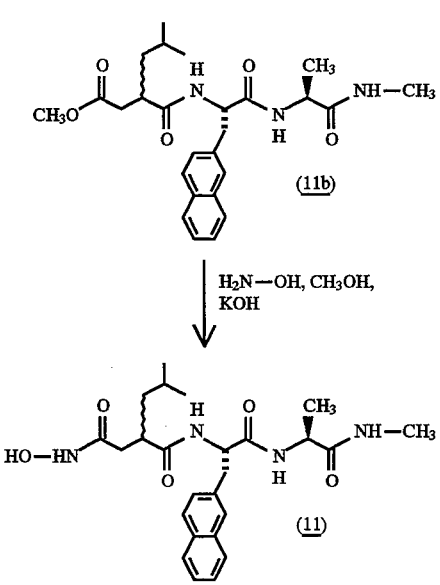

SCHEME 10

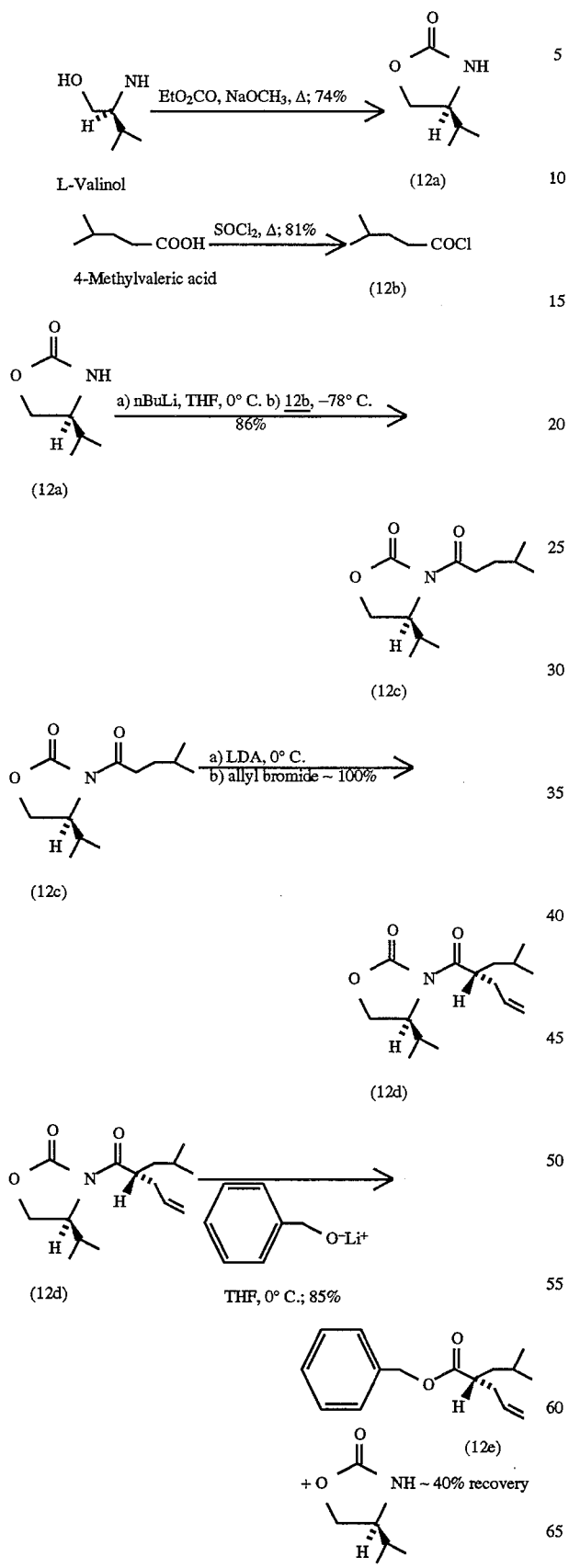

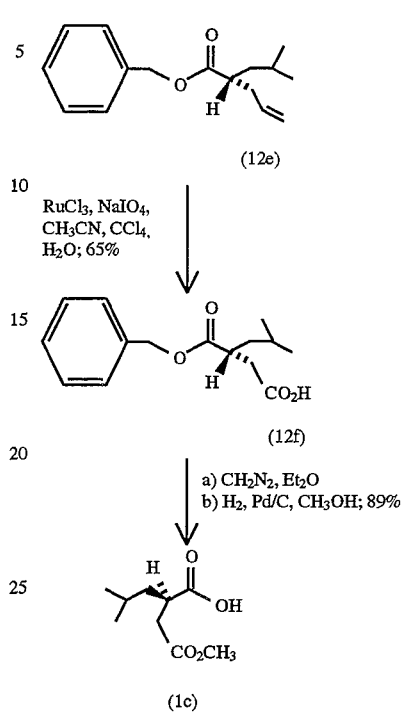

-continued
SCHEME 10

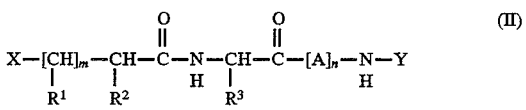

What is claimed is:
1. A method for treating a mammal having a disease characterized by an overproduction or an unregulated production of TNF-α, comprising administering to the mammal a composition comprising an effective amount of a biologically active compound of the formula:

$$X-[CH]_m-\underset{R^2}{CH}-\overset{O}{\underset{\|}{C}}-\underset{H}{N}-\underset{R^3}{CH}-\overset{O}{\underset{\|}{C}}-[A]_n-\underset{H}{N}-Y \quad (II)$$

wherein:

X is hydroxamic acid, phosphoryl or carboxyl;

m is 0, 1 or 2;

$R^1$, $R^2$ and $R^3$ each independent of the other is hydrogen, alkylene(cycloalkyl), $OR^4$, $SR^4$, $N(R^4)(R^5)$, halogen, substituted or unsubstituted $C_1$ to $C_8$ alkyl, $C_1$ to $C_8$ alkylenearyl, aryl, a protected or unprotected side chain of a naturally occurring α-amino acid; or the group —$R^6R^7$, wherein $R^6$ is $C_1$ to $C_8$ alkyl and $R^7$ is $OR^4$, $SR^4$, $N(R^4)(R^5)$ or halogen, wherein $R^4$ and $R^5$ are each, independent of the other, hydrogen or substituted or unsubstituted $C_1$ to $C_8$ alkyl;

n is 1 or 2;

Y is hydrogen, unsubstituted or substituted $C_1$ to $C_8$ alkyl, alkylene(cycloalkyl), the group —$R^8$—$COOR^9$ or the group —$R^{10}N(R^{11})(R^{12})$; wherein $R^8$ is $C_1$ to $C_8$ alkylene; $R^9$ is hydrogen or $C_1$ to $C_8$ alkyl; $R^{10}$ is $C_1$ to $C_8$ alkylene; and $R^{11}$ and $R^{12}$ are each, independent of the other, hydrogen or unsubstituted or substituted $C_1$ to $C_8$ alkyl; provided that when n is 1, A is a protected or an unprotected α-amino acid radical; and when n is 2, A is the same or different protected or unprotected α-amino acid radical; and when n is 2, A is the same or different protected or unprotected α-amino acid radical; and the pharmaceutically acceptable salts thereof;

wherein the compound is capable of reducing serum TNF-α levels by at least 80% when administered at 25 mg/kg in a murine model of LPS-induced sepsis syndrome;

and a pharmaceutically acceptable carrier.

2. The method according to claim 1, wherein B is $C_2$ to $C_6$ alkylene.

3. The method according to claim 2, wherein B is dimethylene.

4. The method according to claim 1, wherein X is hydroxamic acid.

5. The method according to claim 1, wherein $R^1$ is hydrogen or $C_1$ to $C_6$ alkyl.

6. The method according to claim 5, wherein $R^1$ is hydrogen.

7. The method according to claim 1, wherein $R^2$ is hydrogen or $C_1$ to $C_6$ alkyl.

8. The method according to claim 7, wherein $R^2$ is isobutyl.

9. The method according to claim 1, wherein $R^3$ is selected from the group consisting of $C_1$ to $C_6$ alkyl, $C_1$ to $C_6$ alkylenephenol, $C_1$ to $C_6$ alkylene(cycloalkyl) or $C_1$ to $C_6$ alkylenearyl.

10. The method according to claim 9, wherein $R^3$ is $C_1$ to $C_6$ alkyl.

11. The method according to claim 10, wherein $R^3$ is t-butyl.

12. The method according to claim 9, wherein $R^3$ is $C_1$ to $C_6$ alkylenearyl.

13. The method according to claim 12, wherein $R^3$ is methylene-(2'-naphthyl).

14. The method according to claim 1, wherein A is an alanyl or seryl radical, and n is 1.

15. The method according to claim 14, wherein A is alanyl, and n is 0 or 1.

16. The method according to claim 1, wherein the compound is N-{D,L-2-(hydroxyaminocarbonyl)methyl-4-methylpentanoyl}-L-3-(2'-naphthyl)alanyl-L-alanine, 2-(amino)ethyl amide.

17. The method according to claim 1, wherein the compound is N-{D,L-2-(hydroxyaminocarbonyl)methyl-4-methylpentanoyl}-L-3-amino-2-dimethylbutanoyl-L-alanine, 2-(amino)ethyl amide.

18. A pharmaceutical composition for treating TNF-α related disorders, conditions or diseases, comprising an effective amount of a biologically active compound of the formula:

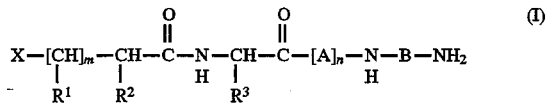

wherein:

X is hydroxamic acid, phosphoryl or carboxyl;

m is 0, 1 or 2;

$R^1$, $R^2$ and $R^3$ each independent of the other is hydrogen, alkylene(cycloalkyl), $OR^4$, $SR^4$, $N(R^4)(R^5)$, halogen, substituted or unsubstituted $C_1$ to $C_8$ alkyl, $C_1$ to $C_8$ alkylenearyl, aryl, a protected or unprotected side chain of a naturally occurring α-amino acid; or the group —$R^6R^7$, wherein $R^6$ is substituted or unsubstituted $C_1$ to $C_8$ alkyl and $R^7$ is $OR^4$, $SR^4$, $N(R^4)(R^5)$ or halogen, wherein $R^4$ and $R^5$ are each, independent of the other, hydrogen or substituted or unsubstituted $C_1$ to $C_8$ alkyl;

n is 1 or 2;

provided that when n is 1, A is a protected or an unprotected α-amino acid radical;

when n is 2, A is the same or different protected or unprotected α-amino acid radical;

B is unsubstituted or substituted C2 to C8 alkylene; and the pharmaceutically acceptable salts thereof.

19. A pharmaceutical composition according to claim 18 further comprising a protein having TNF-α binding activity.

* * * * *